(12) United States Patent
Voldman et al.

(10) Patent No.: US 9,201,060 B2
(45) Date of Patent: Dec. 1, 2015

(54) PARTICLE CAPTURE DEVICES AND METHODS OF USE THEREOF

(75) Inventors: Joel Voldman, Belmont, MA (US); Alison M. Skelley, Medford, MA (US); Oktay Kirak, Boston, MA (US); Rudolf Jaenisch, Brookline, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1302 days.

(21) Appl. No.: 12/867,031

(22) PCT Filed: Feb. 11, 2009

(86) PCT No.: PCT/US2009/033785
§ 371 (c)(1),
(2), (4) Date: Nov. 11, 2010

(87) PCT Pub. No.: WO2009/102783
PCT Pub. Date: Aug. 20, 2009

(65) Prior Publication Data
US 2011/0045994 A1    Feb. 24, 2011

Related U.S. Application Data

(60) Provisional application No. 61/064,008, filed on Feb. 11, 2008.

(51) Int. Cl.
*G01N 33/50* (2006.01)
*B01L 3/00* (2006.01)
*C40B 60/08* (2006.01)
*C12N 5/00* (2006.01)

(52) U.S. Cl.
CPC ...... *G01N 33/5005* (2013.01); *B01L 3/502761* (2013.01); *B01L 2200/0647* (2013.01); *B01L 2200/0668* (2013.01); *B01L 2200/10* (2013.01); *B01L 2200/12* (2013.01); *B01L 2300/0645* (2013.01); *B01L 2300/16* (2013.01); *B01L 2400/0421* (2013.01); *B01L 2400/0424* (2013.01)

(58) Field of Classification Search
CPC ...... G01N 33/5005; B01L 3/502761; B01L 2200/0647; B01L 2200/0668; B01L 2200/10; B01L 2200/12; B01L 2300/0645; B01L 2300/16; B01L 2400/0421; B01L 2400/0424
USPC ...................................... 506/33–40; 435/288
See application file for complete search history.

(56) References Cited

U.S. PATENT DOCUMENTS

| 7,169,578 B2 | 1/2007 | Wang et al. |
| 7,312,085 B2 | 12/2007 | Chou et al. |
| 2006/0128006 A1 | 6/2006 | Gerhardt et al. |
| 2010/0003666 A1* | 1/2010 | Lee et al. ............... 435/5 |

OTHER PUBLICATIONS

Nielsen et al. (J. Microscopy, 2001, 201:368-376).*
Taff et al., "A Scalable Addressable Positive-Dielectrophoretic Cell-Sorting Array," Anal. Chem., 77, pp. 7976-7983 (2005).
International Search Report issued for PCT International Application No. PCT/US09/33785, mailed on Apr. 17, 2009.

* cited by examiner

*Primary Examiner* — Jeremy C Flinders
(74) *Attorney, Agent, or Firm* — Mark S. Cohen; Pearl Cohen Zedek Latzer Baratz LLP

(57) ABSTRACT

The present invention provides a device and methods of use thereof in microscale particle capturing and particle pairing. This invention provides particle patterning device, which mechanically traps individual particles within first chambers of capture units, transfer the particles to second chambers of opposing capture units, and traps a second type of particle in the same second chamber. The device and methods allow for high yield assaying of trapped cells, high yield fusion of trapped, paired cells, for controlled binding of particles to cells and for specific chemical reactions between particle interfaces and particle contents. The device and method provide means of identification of the particle population and a facile route to particle collection.

56 Claims, 5 Drawing Sheets

PARTICLE CAPTURE DEVICES AND METHODS OF USE THEREOF

CROSS-REFERENCE TO RELATED APPLICATIONS

This application is a National Phase Application of PCT International Application No. PCT/US09/33785, International Filing Date Feb. 11, 2009, claiming priority of U.S. Provisional Patent Applications, 61/064,008, filed Feb. 11, 2008, all of which are incorporated herein by reference in their entirety.

GOVERNMENT INTEREST STATEMENT

This invention was made with government support under grant number NAS7-1407 awarded by NASA, and grant numbers R01 EB007278 and 5-R37-CA084198 WIBR awarded by the National Institutes of Health. The government has certain rights in this invention.

FIELD OF THE INVENTION

This invention provides devices and methods of use thereof in particle capturing and particle pairing.

BACKGROUND OF THE INVENTION

Systematic investigation and understanding of small particles and biological cells depends on the tools available with which to probe particle or cell function. An important aspect of cell function is the interaction between two cells. Such interaction occurs at the interface and requires close contact between the two cells. Interaction between cells involves signaling, exchange of membrane material, exchange of intracellular material and fusion of the cells. For particles other than cells, interfacial interaction can result in chemical bonding of two particles and in chemical reactions between two particles. Currently, an ability to capture and pair particles in isolated, defined positions and with high yield is lacking.

The main methods for particle/cell capturing and pairing involve the manipulation of one pair at a time. Usually, one particle/cell is held by one syringe/pipette, and is brought into contact with another cell held at the tip of a second syringe under a microscope. Alternately, one cell can be immobilized on a surface and the other cell will be brought into contact with it using a syringe. Optical trapping of one cell/particle in solution enables the controlled transfer of such cell into contact with another cell that is held by a syringe, an immobilizing surface or an additional optical tweezers. Another method relies on the growth of two neighboring cells until they reach each other and become contacted on a surface.

Large populations of cells/particles can be mixed in solution and get into contact. Solution conditions such as concentration and temperature can enhance such interfacial contact between cells. Chemical functions on cell membranes and on particle surface can cause the binding of cells in solution. However, such binding/contact might be temporary, is not selective, the location of the pairs is not defined and the pairs are not isolated for further analysis.

A device and methods are needed for the specific capturing and pairing of two cells/particles, in predetermined positions, such that the two particles forming a pair are isolated from other pairs, immobilized, their surfaces are in close contact and the identity of each particle is controlled. A device and methods are needed for the observation and manipulation of such pairs. A device and methods are needed for high yield reactions between particle/cell pairs and for the controlled release and collection of the final product or modified cells.

SUMMARY OF THE INVENTION

The invention provides, in one embodiment, a particle capture or particle patterning device, the device comprising:
 a first substrate;
 at least one capture unit positioned such that the top of said capture unit is adhered to or contiguous with said first substrate, said capture unit comprising:
  a first chamber comprising at least one opening, sized to trap and accommodate a single particle; and
  a second chamber comprising at least one opening, sized to trap and accommodate a single or more than a single particle;
 wherein an opening of said first chamber faces a direction opposite to that of an opening of said second chamber, and said opening of said first chamber is contiguous with a side of said capture unit, said opening of said second chamber is contiguous with an opposite side of said capture unit;
  optionally a second substrate positioned proximally to or adhered to a bottom of said capture unit or a portion thereof;
  a conduit through which first flow may be induced in said device, such that fluid flow is accommodated at least between said capture unit and said second substrate and particles positioned within said first or second chamber are subject to said fluid flow; and
  optionally, a second conduit through which a second flow may be induced in a direction opposite to that of said first flow.

In one embodiment, the device further comprises at least one supporting structure positioned between the first and second substrate, which aids in suspending the capture unit over the second substrate, at a height sufficient to accommodate fluid flow between the second substrate and the capture unit.

In one embodiment, at least one supporting structure is proximal to or contiguous with at least a portion of the capture unit.

In one embodiment, the first chamber, second chamber, or a combination thereof comprise at least one additional opening, which is sized such that the opening cannot trap or accommodate one or more particles.

In one embodiment, the additional opening is positioned between the first and second chamber such that the opening facilitates fluid communication between the first and second chamber.

In one embodiment, the particle capturing device further comprises controllers to maintain desirable environmental conditions.

In one embodiment, the controllers maintain a desired temperature, pH, $CO_2$ or oxygen conditions, or a combination thereof.

In one embodiment, the particle capturing device is comprised of a transparent material.

In one embodiment, the transparent material is pyrex, quartz, Polydimethylsiloxane (PDMS) or SU-8.

In one embodiment, the particle patterning device further comprises electric connections between said first capture unit, said second capture unit or a combination thereof and a power supply.

In one embodiment, the particle patterning device is a microfluidic device.

In one embodiment, the first chamber has a width ranging from between 5-500 µm and a depth ranging from between 5-500 µm.

In one embodiment, the first chamber has a width of about 10 µm and a depth of about 5 µm.

In one embodiment, the second chamber has a width ranging from between 5-500 µm and a depth ranging from between 5-500 µm.

In one embodiment, the second chamber has a width of about 10 µm to about 35 µm and a depth of about 5.5 µm to about 50 µm.

In one embodiment, the device comprises an array of capture units, which in one embodiment are positioned in a row or column scheme, or a combination thereof. In one embodiment, the rows, columns or combinations thereof have a spacing there-between approximate in width to a diameter of a particle being applied to the particle patterning device. In one embodiment, capture units are positioned asymmetrically such that a first unit is off-set from that of a second capture unit in a preceding or subsequent row. In one embodiment, the off-set is half the center-to-center distance between two capturing units.

In one embodiment, the invention provides an apparatus comprising the particle patterning device.

In one embodiment, the apparatus comprises an illumination source coupled to the device.

In one embodiment, the illumination source is a laser.

In one embodiment, a beam splitter is employed with the use of the illumination source.

In one embodiment, the apparatus further comprises a detector, which detects a change in a parameter in the device.

In one embodiment, the detector comprises a camera, a computer, a luminometer, a spectrophotometer or a combination thereof.

The invention provides, in one embodiment, a method for patterning individual particles, the method comprising:
(i) applying a first liquid comprising a series of first particles to a particle patterning device under flow in a first direction, whereby an individual particle is accommodated within a first chamber in a first capture unit of said particle patterning device, said device comprising:
  a first substrate;
  at least one capture unit positioned such that the top of said capture unit is adhered to or contiguous with said first substrate, said capture unit comprising:
    a first chamber comprising at least one opening, sized to trap and accommodate a single particle; and
    a second chamber comprising at least one opening, sized to trap and accommodate a single or more than a single particle;
    wherein an opening of said first chamber faces a direction opposite to that of an opening of said second chamber, and said opening of said first chamber is contiguous with a side of said capture unit, said opening of said second chamber is contiguous with an opposite side of said capture unit;
  optionally a second substrate positioned proximally to or adhered to a bottom of said capture unit or a portion thereof;
  a conduit through which first flow may be induced in said device, such that fluid flow is accommodated at least between said capture unit and said second substrate and particles positioned within said first or second chamber are subject to said fluid flow; and
  optionally, a second conduit through which a second flow may be induced in a direction opposite to that of said first flow; and (ii) applying a second liquid to said device under flow in a second direction, wherein said individual particle moves from said first chamber of said first capture unit to a second chamber in a second capture unit.

In one embodiment, the method further comprising the step of applying a third liquid comprising a series of second particles to the device under flow, in the second direction, whereby the series of second particles are captured in the second capture units with the series of the first particles.

In one embodiment, the method further comprises the step of applying a third liquid to the device under flow in the first direction, whereby the individual particle moves back to the first chamber in the first capture unit.

In one embodiment, the series of first particles, second particles or a combination thereof are cells, vesicles, or microspheres or a combination thereof.

In one embodiment, the cells are mammalian cells, bacterial cells, parasitic cells, yeast cells or a combination thereof.

In one embodiment, the series of first particles and the series of second particles comprise cells of a similar cell type or are of, or isolated from, the same organism.

In one embodiment, the series of first particles and the series of second particles comprise cells of a different cell type or are of, or isolated from, a different organism.

In one embodiment, the cells comprise a vector, which optionally comprises a reporter.

In one embodiment, the method is a fusion method between the cells, vesicles or microspheres or a combination thereof.

In one embodiment, the method further comprises applying a reagent to the device under flow in the second direction.

In one embodiment, the reagent is for detection, assay or a combination thereof of the series of first particles, second particles or a combination thereof.

In one embodiment, the reagent comprises a detectable marker.

In one embodiment, the series of first particles and the series of second particles are of the same size.

In one embodiment, the series of first particles and the series of second particles differ in size, composition or a combination thereof.

In one embodiment, the method further comprises the step of observing the series of first particles over a course of time.

In one embodiment, the device is maintained under controlled temperature, pH, $CO_2$, or oxygen conditions, or a combination thereof for the course of time in which the particles are being observed.

In one embodiment, this invention provides a method of contacting individual particles, said method comprising:
(i) applying a first liquid comprising a series of first particles to a particle patterning device under flow in a first direction, whereby an individual particle is accommodated within a first capture unit of said particle patterning device, said device comprising:
  a first substrate;
  at least one capture unit positioned such that the top of said capture unit is adhered to or contiguous with said first substrate, said capture unit comprising:
    a first chamber comprising at least one opening, sized to trap and accommodate a single particle; and
    a second chamber comprising at least one opening, sized to trap and accommodate a single or more than a single particle;
    wherein an opening of said first chamber faces a direction opposite to that of an opening of said second chamber, and said opening of said first chamber is contiguous with a side of said capture unit, said opening of said second chamber is contiguous with an opposite side of said capture unit;

optionally a second substrate positioned proximally to or adhered to a bottom of said capture unit or a portion thereof;

a conduit through which first flow may be induced in said device, such that fluid flow is accommodated at least between said capture unit and said second substrate and particles positioned within said first or second chamber are subject to said fluid flow; and optionally, a second conduit through which a second flow may be induced in a direction opposite to that of said first flow; and (ii) applying flow in a second direction, wherein said individual particle moves from said first chamber of said first capture unit to a second chamber in a second capture unit; and (iii) applying a second liquid comprising a series of second particles to said device in said second direction, whereby said second particles positioned within said second chamber are brought into contact with said series of first particles, thereby being a method of contacting individual particles.

In one embodiment, bringing the first and second series of particles into contact results in a transfer of materials from one particle to another. In one embodiment, the materials comprise a biological material, which in one embodiment is a nucleic acid or polypeptide.

In one embodiment, the particle is a cell, and in another embodiment, the method results in genetic transformation of said cell. In one embodiment, the first or second series of particles or a combination thereof are cells, and in one embodiment, the method comprises a method of cell fusion.

In one embodiment, the method comprises a method of single cell infection and in another embodiment the method comprises a method of phagocytosis.

In one embodiment, bringing the first and second series of particles into contact results in a measurable energy transfer, which in one embodiment is fluorescent resonance energy transfer (FRET).

In another embodiment, the method comprises a screen for molecular interactions.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention provides, in some embodiments, microfluidic capturing devices and methods of use thereof.

I. Particle Capture Devices of the Invention

The invention provides, in one embodiment, a capture-and-pair microfluidic device comprising a first substrate, at least one capture unit positioned such that the top of the capture unit is adhered to or contiguous with the first substrate.

The capture unit comprises: a first chamber comprising at least one opening, sized to trap and accommodate a single particle; and a second chamber comprising at least one opening, sized to trap and accommodate a single or more than a single particle; wherein an opening of the first chamber faces a direction opposite to that of an opening of the second chamber. The opening of the first chamber is contiguous with a side of the capture unit and the opening of the second chamber is contiguous with an opposite side of the capture unit; optionally a second substrate positioned proximally to or adhered to a bottom of the capture unit or a portion thereof; a conduit through which first flow may be induced in the device, such that fluid flow is accommodated at least between the capture unit and the second substrate and particles positioned within the first or second chamber are subject to fluid flow; and optionally, a second conduit through which a second flow may be induced in a direction opposite to that of the first flow.

In some embodiments, the device comprises an array of capture units positioned in rows and/or columns, such that the first chamber is in a first row or column and its opening opposes that of a second chamber, positioned in a subsequent or preceding row or column such that particle transfer from one chamber to another may comprise particle movement from a first row and/or column to another, as desired.

Figure 4:
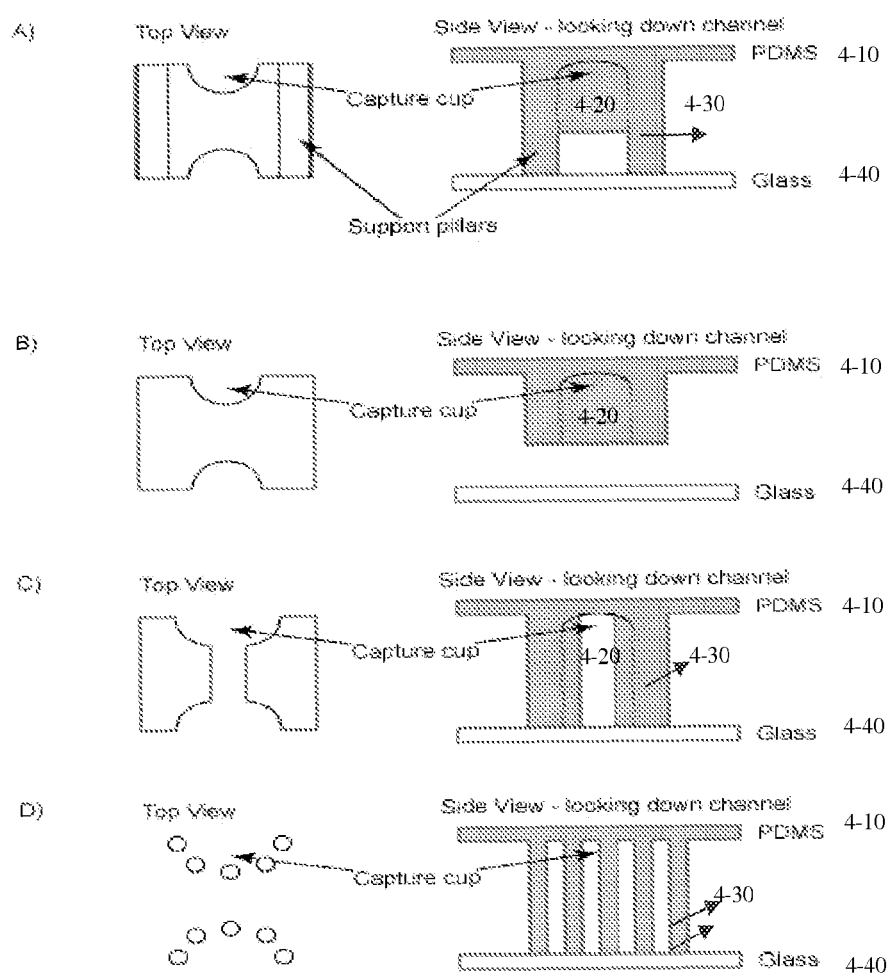
FIG. 4 schematically depicts an embodiment of a device of this invention; a) a weir structure containing capture cups and support pillars to keep the weir from sagging to the surface. In addition to the drawing, capture cups can be V-shaped or square; b) a structure without supports posts; c) a geometry in which the flow-through gap is a vertical gap as opposed to the horizontal gap shown in (a); d) this geometry uses small posts to outline the chambers.

In some embodiment the term "capture unit" refers to the functionality of the unit in trapping or capturing particles in the device. In some embodiment the term "capture unit" refers to a structure which comprises at least two openings in which particles may be trapped or captured. In some embodiments, such a capture unit will comprise two chambers, or two areas in the unit in which particles may be accommodated, with one chamber accommodating only a single particle, referred to herein in some embodiments as the "first chamber" and another accommodating more than the single particle, which is referred to herein in some embodiments as the "second chamber". In some embodiments, the term chamber refers to a unit which is bounded on all sides, with the exception of the indicated opening. In some embodiments, the term "chamber" refers to a structure, which comprises only a single opening large enough to accommodate the indicated particle or particles/size, however it may comprise additional smaller openings. FIG. 4, for example, provides some embodiments of capture units, highlighting the orientation of components of the chambers of this invention, for example, in FIG. 4A or B, the capture unit comprises a bounded chamber, with only a single opening.

In some embodiments, capture units comprise back-to-back positioning of first and second chambers.

FIG. 4 depicts several embodiments of back-to-back positioning of chambers in a capture unit. In some embodiments, the capture units placed back-to-back, or approximately back-to-back, will be in fluid communication, for example as depicted in FIG. 4C, where an additional opening is present in each chamber, where the additional opening is sufficiently large to accommodate fluid or other material transfer from one chamber to another, however it is not sufficient to permit passage of a trapped particle or particles. Similarly in FIG. 4D, a number of openings may be present in each chamber, where the additional openings are sufficiently large to accommodate fluid or other material transfer from one chamber to another, however insufficient to permit passage of a trapped particle or particles.

In some embodiments, the capture unit may comprise two chambers spaced distally from each other, or chambers which are not bonded together by any material. In some embodiments a capture unit of this invention may comprise two chambers, which are not in the same row. In some embodiments a capture unit of this invention may comprise two chambers, which are not in the same column.

In some embodiments the devices will comprise at least one supporting structure, which suspends the capture units over the second substrate, at a height sufficient to accommodate fluid flow at least between the substrate and the capture units, such that particles positioned within the first and/or second chamber of the capture units are subject to fluid flow.

In some embodiments, the supporting structure is adhered to or contiguous with at least a portion of the capture unit. For example, referring to FIG. 4, panel A, wherein the first substrate (4-10) is contiguous with the capture unit (4-20), which is flanked by supporting structures (4-30). The supporting structures extend further than the bounds of the capture unit, such that they contact the second substrate (4-40).

In some embodiments, the device may comprise a supporting structure at any location in the device, which serves to create a distance between the first and second substrate, or the capture unit and the second substrate. For example in FIG. 4B, the supporting pillar is not evident in this scheme; however a space between the capture unit (4-10) and the second structure (4-40) is evident. Such a supporting structure may be a single structure positioned anywhere in the device to effect such an arrangement. For example, in a rectangular device, comprising an array of units, a central supporting structure may be sufficient to achieve the desired spacing between the first substrate/capture unit and the second substrate. In some embodiments, according to this aspect, supporting structures may be positioned at each corner of the device. Other geometries for arrays and devices of the invention may comprise similarly or comparably positioned supporting structures or a single supporting structure, as will be appreciated by the skilled artisan. It is to be understood that any positioning of the supporting structure is envisioned, which achieves a desired spacing of the first substrate/capture unit and the second substrate of the devices of this invention.

In some embodiments, there is no supporting structure, and the first and second substrates are so constructed so as to comprise extensions, which achieve the desired spacing as herein described.

In some embodiments capture units of this invention will comprise more than a single opening to accommodate fluid communication between the trapped particle and fluid flowed over the second substrate. In some embodiments, such openings may comprise a slit, or large spacings, or any arrangement which allows fluid flow in the device, and fluid communication of the particles with the fluid applied to the device, such that particles can, in some embodiments, be subject to flow.

In some embodiments, this invention provides a patterning device comprising a first substrate onto which capture units are constructed, or in some embodiments, the capture units are contiguous with the first substrate, or in some embodiments, the capture units are bonded or adhered to the first substrate.

In one embodiment the first, the second, or both substrates are flexible. In one embodiment the first, the second, or both substrates are rigid.

In one embodiment the first, the second, or both substrates are flat. In one embodiment the first, the second, or both substrates are curved. In one embodiment the substrate is curved to a cylindrical shape or a closed tube shape. In one embodiment, capture units are patterned on an inner surface of a tubed substrate. In one embodiment fluid flows in the direction of a long axis of the tubed substrate. According to this aspect, and in one embodiment, the capture unit comprises chambers positioned back-to-back, such that the top and bottom of the capture unit abut the tubed-substrate, such that the device comprises only a first substrate.

In one embodiment the first and the second substrate are comprised of the same material. In some embodiments the first and the second substrate are comprised of different materials.

In one embodiment, a device of this invention may comprise parallel-positioned substrates comprising capture units, within a single device, such that each substrate is spaced sufficiently from one another such that fluid flow applied to the device flows over each substrate enabling greater patterning/capture efficiency in a larger number of capture units per volume of the total device. In one embodiment, a flexible substrate patterned with capture units is folded to a desired shape, for example, in a spiral shape to increase the number of capture units per volume of device. In some embodiments multiple tubular patterned substrates are packed in parallel in a device. It is to be understood that any orientation in the device of substrates comprising patterning units, or second substrates covering the device may be effected, and such devices are to be considered as part of this invention.

In one embodiment the device may comprise a substrate comprising capture units positioned on both sides of the substrate, or on any side of the substrate, or on all sides of the substrate. In one embodiment patterning of capture units on multiple external sides or internal sides of the substrate increases the number of capture units, and in some embodiments, the operating efficiency of the device, or in some embodiments, conserves the amount or reagent or particles or other materials needed for use in such devices.

In one embodiment the number of substrates comprising capture units within a device of the invention is a factor of the dimensions of the device, or in some embodiments, the applications for use of the device, or in some embodiments, the types or dimensions of particles being captured. In some embodiments, any number of substrates may be positioned in the device, for example, ranging from about 1-10,000. In some embodiments, the number of substrates comprising capture units per device ranges between 1-10. In one embodiment the number of substrates per device ranges between 10-100. In one embodiment the number of substrates per device ranges between 10-50. In one embodiment the number of substrates per device ranges between 100-1000. In one embodiment the number of substrates per device ranges between 1000-10000. In one embodiment the number of substrates per device ranges between 1000-3000.

In one embodiment the substrate comprises micro or nano wires. In one embodiment the substrate comprises electrical conducting micro or nano wires. In one embodiment the electrical wiring connects the capture units to contacts at the periphery of the substrate. In one embodiment the micro- or nano-wires in the substrate are optical fibers. In one embodiment the optical fibers generates or collects optical signals to or from the capture unit and their contents.

Flow is induced in the devices of this invention. In some embodiments, flow is induced by the application of a pump, a syringe, a piston or a combination thereof. In one embodiment the flow is pressure driven and in another embodiment the flow is driven by osmosis, or the flow is an electro-osmotic flow. In some embodiments flow is induced by capillary forces. In some embodiment the unit to induce flow comprises or is connected to adaptors, a power supply, pressure gauges, water reservoirs, a vacuum pump, flow controllers, flow timers, sealing accessories, plastic tubing and/or temperature controllers.

In some embodiments, the devices of this invention comprise a conduit through which flow may be induced in the device. In some embodiments, the term "conduit" with reference to inducing flow may refer to an inlet to which a device which induces flow is attached, for example a syringe or pump, which may be attached directly to the inlet, or in some embodiments, via an adaptor, a filter, or any other desired material, as will be appreciated by the skilled artisan. In some embodiments, the conduit is an opening in the device, or in some embodiments, the device is sealed around the unit or device inducing flow such that a seal between the device and the unit inducing flow is accomplished. In some embodiment, flow is electroosmotically driven and the conduit refers to the positioning of electrodes, etc., inducing an electric field in the device in order to produce electroosmotic flow in the device upon delivery of an electrolyte-containing fluid to the device. It is to be understood that any structuring of the device to accommodate a unit or means to induce flow in the device is what is to be understood as encompassed by the phrase "a conduit through which fluid may be induced", and is part of the present invention.

In some embodiments flow refers to liquid, solution or fluid flow. In one embodiment flow is an air or gas flow, or flow of an aerosol or gaseous mixture of particles. In one embodiment fluid flow is followed by air/gas flow. In some embodiments subsequent air/gas flow is used to clean, manipulate or treat the trapped particles or the device.

In some embodiments, flow is induced in a single direction, and the devices of this invention may readily be inverted to induce flow in an opposing direction. In some embodiments, flow is induced in two directions in the device.

The capture units are suspended over the second substrate in some embodiments. The term "suspended over" refers, in some embodiments to the orientation of capture units such that the chamber openings in the capture units face or oppose, respectively the direction of flow induced in the device, and these are contiguous with or correspond to the sides of a capture unit. The side of the chamber most distal to the opening of the chamber is in some embodiments attached to, or proximal to a suspending post, which allows for suspension of the capture units. In some embodiments, the side of the chamber parallel to and nearest the first substrate surface, is the top of the capture unit, whereas the side of the chamber parallel to and furthest from the first substrate surface is the bottom of the capture unit. In some embodiments, the side of the chamber most proximal to the second substrate is in some embodiments attached to a suspending post, which allows for suspension of the capture units. In some embodiments, the side of the chamber parallel to and nearest the second substrate surface, is attached or bound to the second substrate by suspending posts. In some embodiments two suspending posts are attached to the second substrate and to the chambers.

In some embodiments, the suspending posts may have any desired shape, and in some embodiments, such choice will reflect the type of flow induced in the device, and optimization of flow in the device. In some embodiments the suspending posts have a rectangular shape. In some embodiments the two suspending posts have the shape of a rod. In one embodiment the suspending posts are rounded. In one embodiment the two suspending posts and the two chambers comprises a capture unit. In some embodiments the two suspending posts have spacing therebetween. In some embodiments the spacing allows for flow underneath the chambers and on top of the second substrate. In some embodiments the capture units are suspended on supporting pillars such that a gap is formed between the second substrate and the bottom of the capture units to enable fluid flow. In some embodiments the dimensions of the supporting pillars are 7 µm wide×30 µm deep×8 µm tall. In one embodiment the supporting structure has a width of about 1-15 µm, a length of about 10-50 µm and a height of about 1-15 µm. In some embodiments the width, depth, height or a combination thereof of the supporting pillars ranges between 10-100 nm. In some embodiments the width, depth, height or a combination thereof of the supporting pillars ranges between 100-1000 nm. In some embodiments the width, depth, height or a combination thereof of the supporting pillars ranges between 1-10 µm. In some embodiments the width, depth, height or a combination thereof of the supporting pillars ranges between 10-100 µm. In some embodiments the width, depth, height or a combination thereof of the supporting pillars ranges between 0.1-100 µm. In some embodiments the width, depth, height or a combination thereof of the supporting pillars ranges between 50-100 µm.

In some embodiments the total distance between the first and the second substrates is the sum of the heights of the capture units and the supporting pillars. In some embodiments the total distance between the first and the second substrates is of the order of 1-2 particle diameters. In some embodiments the total distance between the first and the second substrates is of the order of 1-5 particle diameters. In some embodiments the total distance between the first and the second substrates is 20 microns. In some embodiments the total distance between the first and the second substrates ranges between 1-200 microns. In some embodiments the total distance between the first and the second substrates ranges between 1-100 nm. In some embodiments the total distance between the first and the second substrates ranges between 10-1000 nm. In some embodiments the total distance between the first and the second substrates ranges between 1-10 µm. In some embodiments the total distance between the first and the second substrates ranges between 10-1000 µm, and in other embodiments between 500-1000 µm.

In some embodiments, the distance between the first and the second substrates are designed to minimize effects on particles trapped therewithin. In some embodiments, the chamber orientation and dimension and shape are such to minimize impact of the deposition of particles therewithin, in particular in terms of flow-driven effects.

In some embodiments, the device comprises a closed system, having two substrates positioned in parallel, with capture units placed therebetween. According to this aspect, and in some embodiments, the capture units are attached to supports or to suspending posts bound to one of the two substrates, and flow is induced such that liquid is flowed over the surface of the second of the two substrates. According to this aspect, and in some embodiments, the capture units are filled with a particle, which is suspended over the second substrate, in the liquid applied to the device and thereby trapped, yet flow is not perturbed by the supports or the suspending posts.

In some embodiments, the suspending posts are an example of a supporting structure in the device, which suspends the capture units over the substrate, at a height sufficient to accommodate fluid flow at least between the substrate and the capture units, such that particles positioned within said first or second chamber are subject to the fluid flow.

In some embodiments two chambers are positioned back to back, with openings in or against the direction of fluid flow, wherein an opening of the first chamber faces a direction opposite to that of an opening of the second chamber and wherein the first chamber has a depth which accommodates a single particle and the second chamber has a depth which accommodates a single or more than a single particle;

In some embodiments the two chambers are elevated from the second substrate surface by two supporting structures patterned in a polydimethylsiloxane (PDMS) substrate.

In some embodiments the chamber has dimensions on a micron scale. In some embodiments the first chamber that has a depth which accommodates a single particle is smaller than the second chamber that has a depth which accommodates a single or more than a single particle. In some embodiments the dimensions of the first chamber are 10 µm wide×5 µm deep×12 µm tall and the dimensions of the second chamber are 18 µm wide×25 µm deep×12 µm tall.

In one embodiment, the first chamber has a width ranging from between 5-500 µm and a depth ranging from between 5-500 µm. In one embodiment, the first chamber has a width of about 10 µm and a depth of about 5 µm. In one embodiment, the second chamber has a width ranging from between 5-500 µm and a depth ranging from between 5-500 µm. In one embodiment, the second chamber has a width of about 10 µm to about 35 µm and a depth of about 5.5 µm to about 50 µm.

In some embodiments the width, depth or height or a combination thereof of the first chambers, the second chambers or a combination thereof ranges between 1-10 µm. In one embodiment the width, depth or height or a combination thereof of the first chambers, the second chambers or a combination thereof ranges between 10-100 µm. In one embodiment the width, depth or height or a combination thereof of the first chambers, the second chambers or a combination thereof ranges between 1-50 µm. In one embodiment the width, depth or height or a combination thereof of the first chambers, the second chambers or a combination thereof ranges between 0.1-10 µm. In one embodiment the width, depth or height or a combination thereof of the first chambers, the second chambers or a combination thereof ranges between 0.01-1 µm. In one embodiment the width, depth or height or a combination thereof of the first chambers, the second chambers or a combination thereof ranges between 0.001-10 µm. In one embodiment the width, depth or height or a combination thereof of the first chambers, the second chambers or a combination thereof ranges between 1-1000 µm. In one embodiment the width, depth or height or a combination thereof of the first chambers, the second chambers or a combination thereof ranges between 10-500 µm. In one embodiment the difference in size between the first and second chambers is only incremental. In one embodiment the second chamber is only slightly larger than the first chamber. In one embodiment the depth of the first chamber is 5 microns and the depth of the second chamber is 5.1 micron. In one embodiment the depth of the first chamber is 5 microns and the depth of the second chamber is 5.5 microns. In one embodiment the width of the first chamber is 10 microns and the width of the second chamber is 10.1 micron. In one embodiment the width of the first chamber is 10 microns and the width of the second chamber is 10.5 microns. In one embodiment the second chamber accommodates a single particle and in another embodiment the second chamber accommodates more than a single particle. In one embodiment the second chamber accommodates two particles, wherein the size of the second particle is 1% of the size of the first particle. In one embodiment the second chamber accommodates two particles, wherein the size of the second particle is 50% of the size of the first particle. In one embodiment the second chamber accommodates two particles which are comparable in size.

In one embodiment the chambers are used to trap single mammalian cells, and the chamber(s) dimensions for width, length, height, etc. ranges from between 10-70 micron. In another embodiment the chambers are used to trap single bacterial cells and the chamber dimensions for width, length, etc., ranges from between 1-10 microns. In one embodiment the chambers are used to trap nanoparticles and the chamber dimensions for width, length, height, etc. ranges between 1 nm and 1000 nm. In another embodiment the chambers are used to trap large vesicles and the chamber dimensions for width, length, height, etc. ranges from between 1-100 microns. In another embodiment the chambers are used to trap small vesicles and the chamber dimensions for width, length, height, etc. ranges from between 1-100 nm or between 10-1000 nm.

In some embodiments the chamber has a U-shape. In some embodiments the chamber has a triangular shape open on one side. In one embodiment the chamber has a square or rectangular shape open on one side. In some embodiments, the shape of the chamber may be specific to facilitate trapping of the desired cell or particle. For example and in some embodiments, the chambers have round bottom for capturing cells or liposomes. For example and in some embodiments, the chambers have a triangular shape to trap rods or cocci. In some embodiments the chambers have an opening that is larger in dimensions from the bottom of the chambers to facilitate transfer of particles from the chamber. In some embodiments the chambers have opening that is smaller in dimensions from the bottom of the chamber to delay transfer of particles from the chamber. In one embodiment facilitating transfer from the chamber is desired for first chambers, and delaying transfer from a chamber is desired for second chambers.

In some embodiments the devices of the invention comprise an array of capture units. In some embodiments the array comprises rows and/or columns. In one embodiment the spacing between two capture units in a row and/or column and/or the spacing between two rows/columns is comparable to about the diameter of one or two particles being captured. In one embodiment spacing of the order of a particle diameter, enhances the probability of particle capture, while maintaining continuous flow of particles through the device. In one embodiment the spacing between two capture units in a row and/or the spacing between two rows is 40 microns. In one embodiment the spacing between two capture units in a row and/or the spacing between two rows ranges between 1-50 microns. In one embodiment the spacing between two capture units in a row and/or the spacing between two rows ranges between 50-200 microns. In one embodiment the spacing between two capture units in a row and/or the spacing between two rows ranges between 0.001-1 microns. In one embodiment the spacing between two capture units in a row and/or the spacing between two rows ranges between 0.01-10 microns.

In some embodiments, device dimensions and capture unit positioning within the device will be such that the device is easily integrated into existing automated apparatuses, for example, within ELISA readers, or other optical-based automated detection systems.

In some embodiments there is an off-set between neighboring rows. In some embodiments the off-set is half the center-to-center distance between two neighboring units in a row. In one embodiment rows are staggered.

In some embodiments the off-set between neighboring rows results in a diagonal placement of any capture unit in row n with respect to the two closest capture units of row (n+1). In some embodiments any capture unit in row n and two closest capture units of row (n+1) represent the corners of a triangle. In some embodiment the off-set results in having capture unit of row n in the same column of capture unit of row (n+2). In some embodiments the off-set results in a configuration such that the opening of the second chamber of row n, faces the opening of the first chamber of row (n+2). In some embodiments such configuration allows easy trapping of particles in the first chamber. In some embodiments such configuration enables the direct transfer of particles from a first chamber in row (n+2) to a second chamber in row n. In some embodiments the configuration allows easy trapping of a second particle in a second chamber. In some embodiments such configuration allows for a smooth fluid flow. In some embodiments the direction of the fluid flow can be reversed. In some embodiment the fluid flow can enter a first flow inducing unit and exit through a second flow inducing unit, and in some embodiments the fluid flow can be reversed such that it enters through the second flow inducing unit and exit through the first flow inducing unit. In one embodiment, the flow is electro-osmotic, or in another embodiment, the flow is pressure driven. In some embodiments fluid can contain particles or cells and in some embodiment the fluid can be a particle-free media.

In some embodiments the capture units, chambers, supporting pillars and spaces between them are scalable to nanometers and the particles of interest are nano-sized particles.

In one embodiment the number of capture units in a device is any that is suitable for a particular application. In some embodiments, such number will be a reflection of the dimension of the device and capture units and the scale employed. In some embodiments, the number of units ranges from between 1-10. In one embodiment the number of capture units per device is ranges from between 1-1000. In one embodiment the number of capture units per device ranges from between 10-100. In one embodiment the number of capture units per device ranges from between 100-200. In one embodiment the number of capture units per device ranges from between 100-500. In one embodiment the number of capture units per device ranges from between 500-1000. In one embodiment the number of capture units per device ranges from between 1000-10000. In one embodiment the number of capture units per device ranges from between 5000-10000. In one embodiment the number of capture units per device ranges from between 200-750.

In some embodiments, the substrate, chambers, capture units, suspension pillars or a combination thereof comprise a material, which is suitable for any manipulation or condition in which particle patterning using the devices of this invention is desired. In some embodiments, the substrate, chambers, capture units, suspension pillars or a combination thereof comprise any suitable polymer.

In one embodiment the substrate, capture units, suspension pillars or a combination thereof comprise an inorganic material. In some embodiments the inorganic material is silicon. In one embodiment the inorganic material is silicon dioxide or silicon nitride or silicon coated by silicon dioxide or silicon nitride. In one embodiment the inorganic material is titanium oxide, indium oxide or indium tin oxide. In one embodiment, the inorganic material is a metal or a metal alloy. In one embodiment the inorganic material is gold, Ti/gold, Pt, Pd, or gold/palladium. In one embodiment the inorganic material is glass, pyrex or quartz.

In one embodiment the substrate, capture units, suspension pillars or a combination thereof are made of a semiconducting material. In some embodiments the semiconducting material is doped. In one embodiment the doping is n-type and in another embodiment the doping is p-type.

In one embodiment the substrate, capture units, suspension pillars or a combination thereof are made of a transparent material. In one embodiment the transparent material is or SU-8.

In one embodiment, the substrate and/or other components of the device can be made from a wide variety of materials including, but not limited to, silicon, silicon dioxide, silicon nitride, glass and fused silica, gallium arsenide, indium phosphide, III-V materials, PDMS, silicone rubber, aluminum, ceramics, polyimide, quartz, plastics, resins and polymers including polymethylmethacrylate (PMMA), acrylics, polyethylene, polyethylene terephthalate, polycarbonate, polystyrene and other styrene copolymers, polypropylene, polytetrafluoroethylene, superalloys, zircalloys, steel, gold, silver, copper, tungsten, molybdenum, tantalum, Kovar, Kevlar, Kapton, Mylar, Teflon, brass, sapphire, other plastics, or other flexible plastics (polyimide), ceramics, etc., or a combination thereof. The substrate may be ground or processed flat. High quality glasses such as high melting borosilicate or fused silicas may be used, in some embodiments, for their UV transmission properties when any of the sample manipulation and/or detection steps require light based technologies. In addition, as outlined herein, portions of the internal and/or external surfaces of the device may be coated with a variety of coatings as needed, to facilitate the manipulation or detection technique performed.

In another embodiment, the substrate and/or chambers of the devices of this invention comprise a material which is functionalized to minimize, reduce or prevent adherence of materials introduced into the device. For example, in one embodiment, the functionalization comprises coating with extracellular matrix protein/s, amino acids, PEG, or PEG functionalized SAM's or is slightly charged to prevent adhesion of cells or cellular material to the surface. In another embodiment, functionalization comprises treatment of a surface to minimize, reduce or prevent background fluorescence. Such functionalization may comprise, for example, inclusion of anti-quenching materials, as are known in the art. In another embodiment, the functionalization may comprise treatment with specific materials to alter flow properties of the material through the device. In another embodiment, such functionalization may be in discrete regions, randomly, or may entirely functionalize an exposed surface of a device of this invention.

In some embodiments the substrate, capture units, suspension pillars or a combination thereof are opaque. In one embodiment the substrate, capture units, suspension pillars or a combination thereof are partially transparent, allowing the transmittance of parts of the electromagnetic radiation range. In some embodiments the transmitted electromagnetic radiation range is in the IR, UV, Visible, Microwave range or a combination thereof.

In some embodiments, the substrate, capture units, suspension pillars or a combination thereof are constructed of a material which renders it transparent or semitransparent, in order to image the materials being assayed, or in another embodiment, to ascertain the progress of the assay, etc. In some embodiments, the materials further have low conductivity and high chemical resistance to buffer solutions and/or mild organics. In other embodiments, the material is of a machinable or moldable polymeric material, and may comprise insulators, ceramics, metals or insulator-coated metals. In other embodiments, the capture unit/substrate may be constructed from a polymer material that is resistant to alkaline aqueous solutions and mild organics. In another embodiment, the capture unit/substrate comprises at least one surface which is transparent or semi-transparent, such that, in one embodiment, imaging of the device is possible.

In one embodiment the substrate, capture units, suspension pillars or a combination thereof are coated or covered. In one embodiment the coating comprises a monolayer. In one embodiment the monolayer comprises organic molecules. In one embodiment, the organic molecules comprise a functionalized end group.

In one embodiment the organic molecules comprise two functional end groups. In one embodiment one functional group binds the molecule to the capture unit material and the second functional unit is exposed. In one embodiment the second functional group is hydrophobic. In one embodiment the second functional group is hydrophilic. In one embodiment the exposed functional group prevents cell adhesion, In one embodiment the exposed functional group promotes cell adhesion. In one embodiment the exposed functional group binds cells or particles within chambers. In some embodiments the capture units are coated by an inorganic material. In one embodiment the inorganic material is an oxide layer. In one embodiment the inorganic material is a metal. In one embodiment the coating is gold. In one embodiment the coating is polar. In one embodiment the coating is non-polar. In one embodiment the coating is electrically conducting. In one embodiment the coating is electrically insulating or semiconducting. In one embodiment the coating is heat conducting. In one embodiment the coating reduces heat transfer. In one embodiment the coating of the capture units is achieved by exposure to oxygen or other gaseous molecules. In one embodiment coating is done by electrodeposition, by electroless deposition, by chemical vapor deposition, by sputtering, metal evaporation, spin-coating or self-assembly. In one embodiment the substrate, capture units, suspension pillars or a combination thereof are magnetized to attract metallic particles.

In another embodiment, the coating material is a low-autofluorescent material. In another embodiment, the entire array is, and in another embodiment, the array with the exception of the vessels, is coated with a microstamping material. In one embodiment, the microstamping material is polyethylene glycol or octadecyl-trichlorosilane. In another embodiment, the coating material is a positively charged material. In another embodiment, the coating material comprises at least one protein, which, in another embodiment, is an extracellular matrix protein.

In one embodiment, the substrate, capture units, suspension pillars or a combination thereof are coated with a material, which minimizes particle adhesion thereto, which in one embodiment is teflon, or in another embodiments, is a protein solution, which in one embodiment, comprises Bovine Serum Albumin (BSA).

In one embodiment, to prevent non-specific cell adsorption the substrate, and supporting pillars, or a combination thereof but not the inner part of the chambers may be coated, by microstamping molecules such as polyethylene glycol (PEG) or octadecyl-trichlorosilane (OTS), both of which resist protein adhesion and are commonly used for confining cells. According to this aspect, in some embodiments, because the cells will be trapped within chambers, using a blank microstamp to coat the surface will leave the inner part of the chambers uncoated, as desired. In some embodiments, the substrate, supporting pillars, chambers or a combination thereof may then be flooded with fibronectin or other ECM molecules to enhance cell attachment to the inner part of the chambers. In some embodiments, the protein-inhibiting surface may also reduce any potential fouling of the device.

In one embodiment the device has dimensions 1 cm$^3$. In one embodiment the width, length, and height of the device or a combination thereof ranges between 1-10 cm. In one embodiment the width, length, and height of the device or a combination thereof ranges between 1-10 µm. In one embodiment the width, length, and height of the device or a combination thereof ranges between 10-1000 µm. In one embodiment the width, length, and height of the device or a combination thereof ranges between 500-750 µm. In one embodiment the width, length, and height of the device or a combination thereof ranges between 1-10 cm, or in some embodiments, 10-100 mm. In one embodiment the width, length, and height of the device or a combination thereof ranges between 100-450 µm. In one embodiment the width, length, and height of the device or a combination thereof ranges between 0.1-1 µm. In one embodiment the width, length, and height of the device or a combination thereof ranges between 1-10 nm.

It is to be understood that the devices of this invention may be of any dimension suitable for particle trapping and/or patterning, to suit any application, and the dimensions described serve for exemplification purposes alone. The devices of this invention are envisioned for use in micro- and nano-fluidic applications, in some embodiments, or for use with standard tissue culture dish automated reader applications. For example in some embodiments, the device may approximate 96-well culture plates, or 48 well culture plates, or 24 culture plates, with chamber sizes appropriate for capture of single cells which in turn remain in the device over time, where clonal colonies are obtained, for example with use in hybridoma technology, or for example for use in stem cell engineering applications, for the formation of spheroids or other desired structures.

In one embodiment the devices of this invention are maintained under controlled temperature, pH, $CO_2$ or Oxygen conditions, or a combination thereof.

In one embodiment the device is disposable or in another embodiment, sterilizable.

In one embodiment capture of particles in the devices of this invention is achieved with high yield.

In one embodiment the invention provides capture devices, kits comprising the same and methods of use thereof for immobilizing two or more particles and for bringing them into contact. In some embodiments, a capture unit is used to trap and immobilize the particles. In one embodiment the at least two particles are trapped consecutively in a capture unit. In one embodiment, consecutive trapping of particles enables the selection of the particle identity.

In one embodiment consecutive trapping of particles enables sequential particle trapping, such that particles of a first type are trapped prior to those of a second type. In one embodiment such consecutive trapping enables close contact between two different particles. In one embodiment such pairing of particles can be useful for synthesis, for particle modifications, for cell fusion, for studies of infection, etc.

In one embodiment pairing of particles is achieved with high yield. In one embodiment trapping and pairing of particles is achieved with high efficiency. In one embodiment ~80% of the second chambers contain exactly two cells, or more, when successive rounds are undertaken to add cells to the second chambers, as will be understood by the skilled artisan. In one embodiment >50% of the chambers contain properly paired cells.

In some embodiments such consecutive trapping can involve any number of particles, for example, two or more particles. In one embodiment a step-by-step chain process can be performed on a single particle, or series of particles, using the device and methods of the invention. In some embodiments, the first particle is immobilized or attached to a wall of the chamber following transfer to the second chamber, while subsequent particles are not adhered, such that sequential interaction of subsequent particles with a first particle may be effected.

The devices of this invention, in some embodiments, make use of a microfabricated array of capture units, which enables, in some embodiments, the isolation of two particles in each unit. The capture-and-pair process is fast, straightforward and inexpensive, and the large array of capture units provides high yield of particle pairs, which in the past was difficult to obtain. Observation and manipulation of the particle pairs is simple due to the predetermined positions of the capture units.

II. Processes to Prepare Capture Devices of the Invention

In some embodiments the capture units are patterned on the substrate. In some embodiments the capture units are patterned using lithography and etching processes. In one embodiment lithography is UV, X-ray or electron beam lithography. In one embodiment patterning is carried out using soft-lithography, stamping, embossing, imprinting or patterning using an AFM or an STM tip. In some embodiments device processing involves etching. In one embodiment etching is dry. In one embodiment etching is wet. In one embodiment etching is material-selective. In one embodiment a mask is used to protect some areas of the device from being etched. In one embodiment the substrate with the capture units or the capture units alone are patterned using a mold or a template. In one embodiment the capture units are glued, bonded, soldered or welded to the substrate. In one embodiment coating or layering of the device or of elements in the device is carried out by exposure to oxygen or other gaseous molecules. In one embodiment coating is done by electrodeposition, by electroless deposition, by chemical vapor deposition, by sputtering, metal evaporation, spin-coating or self-assembly.

In some embodiments, the devices and methods of this invention entail patterning a Polydimethylsiloxane (PDMS) substrate to form an array of capture units. The patterned PDMS substrate serves as the top of the microfluidic channel. In some embodiments, the microchannel fabrication is completed via e.g. plasma bonding the PDMS patterned first substrate to a second glass substrate. In some embodiments the first patterned substrate is plasma bonded to a second silicon or a silicon dioxide substrate. In some embodiment the first and second substrates are sealed together by the chemical adherence properties between the two substrates. In some embodiments adherence of the first substrate to glass, polystyrene or to silicon is reversible. In some embodiment one type of second substrate can be attached to the first substrate. The second substrate can be later removed and replaced by another type of second substrate. In one embodiment the first and second substrates are clamped. In one embodiment clamping provides efficient and reversible sealing method for the device. In one embodiment an array of patterned substrates are packed into one device. In one embodiment the array is made of parallel planar substrates. In one embodiment the array is made of closely packed cylindrical substrates. In one embodiment the array is packed using spacers between substrates. In one embodiment the spacer are pre-patterned into points or areas in the substrate. In one embodiment the spacers are introduced onto the substrate after the substrate is patterned.

III. Apparatuses/Kits Comprising the Particle Capture and Pair Devices of the Invention In some embodiments, this invention provides a kit comprising a device of this invention and optionally particles and reagents for use with the kit. In some embodiments, the devices/kits of this invention are modular in design such that they can be incorporated into larger apparatuses, to which other necessary devices or machineries are coupled. For example, the device comprises inlets/adaptors to which a flow-generating device may be operationally coupled, or for example a power source for the application of an electric field to the device, etc.

In one embodiment the modular device is constructed such that an array of light sources and detectors may readily be coupled thereto. In some embodiments the light sources are laser sources, visible or UV sources or IR sources. In some embodiments the array of chambers in the device overlap with an array of electrical contacts patterned on the device or proximally or operationally connected to the device, such that the contacts supply or detect electrical parameters of the chamber contents.

In some embodiments, electromagnetic radiation excitation of the trapped particles is conducted in conjunction with electrical excitation or detection.

In one embodiment the modular device is designed such that it fits onto a microscope moving stage, and individual chambers of the device may be imaged or viewed. In some embodiments the microscope stage is automated. In some embodiments the contents of the chambers can be observed in a parallel or a serial manner using the automated microscope stage. In some embodiments, the first or second substrate is of a thickness that any desired optical application may be effected, for example, in some embodiments, the device cover may be constructed of a coverglass, such that confocal imaging of the trapped particles is practical.

In one embodiment the kit comprises a pressure control gauge. In one embodiment the kit comprises at least one syringe. In one embodiment the kit comprises an injection system. In one embodiment the injection system is automated. In one embodiment the injection system comprises a robot. In one embodiment the injection system comprises an automated pipetor. In one embodiment a series of devices or device arrays of the present invention can be injected with fluids or solutions in a parallel manner.

In one embodiment, the devices may be coupled to a micropipetor, such that microinjection of trapped cells or vesicles is readily accomplished. According to this aspect, and in some embodiments, such devices may be so constructed so as to effectively trap non-adherent cells for microinjection, which at present is not accomplished with high efficiency. In some embodiments, such microinjection methods offer an advantage in that minimal cell manipulation occurs for microinjection of non-adherent cells in this aspect.

In some embodiments, electroporation of trapped individual cells, or clusters of cells, or colonies of cells may be accomplished, and in one embodiment, transformation efficiency may thus be enhanced by utilizing the devices of the invention.

In one embodiment the kit comprises of at least one vessel to accumulate the solution exiting the device or the device array. In one embodiment the vessel is a vial, a test tube, an eppendorf, a 96 well array, a petri dish or a sterilized bottle. In one embodiment the kit comprises a temperature control gauge. In one embodiment the kit comprises a temperature control system. In one embodiment the temperature control system comprises a heating element. In one embodiment the temperature control system comprises a coolant. In one embodiment the coolant comprises a liquid. In one embodiment the cooling system is an air-cooling system. In one embodiment the cooling system comprises a fan. In one embodiment the device is wrapped in the temperature control system. In one embodiment the temperature control system is built into the substrate and capture units. In some embodiments the temperature control system is in the form of hollow channels or solid channels carved in or webbed through the device.

In one embodiment the apparatuses/devices/kits of this invention comprise/accommodate incorporation of a light source, a detector or a combination thereof. In one embodiment the light source is a UV or visible source. In one embodiment the light source is in the IR range. In one embodiment the light source comprises a lamp. In one embodiment the light source comprises a laser. In one embodiment the light source is pulsed and in another, continuous.

In one embodiment the apparatuses/devices/kits of this invention comprise/accommodate incorporation of a detector mounted opposite the light source. In one embodiment the detector comprises a CCD camera. In one embodiment the detector is further connected to a computer. In one embodiment the light source and detector are part of an optical microscope. In one embodiment the detector is a digital camera. In one embodiment the detector is a video camera.

According to this aspect and in one embodiment, light passes through at least one capture unit and reaches the detector. In one embodiment the detector can read the content of the capture unit. In one embodiment the detector reads an optical signal coming from the capture unit and turns it into an image or into a light intensity data. In one embodiment the detector is connected to a processing system. In one embodiment the detector, computer, processing system, microscope, an operator or combination thereof can get information regarding the content of the capture unit. In one embodiment a feedback reaction takes place after optical data is taken and processed. In one embodiment the reaction comprises the introduction of fluid, dispensing fluid, adding chemicals, changing temperatures, changing optical or electrical parameters affecting the contents of the device of this invention. In one embodiment the detector comprises a fluorescent light detector. In one embodiment the particles trapped in the capture units are fluorescent or contain fluorescent markers. In one embodiment the fluorescent marker is fluorescein, a quantum dot or a green fluorescent protein (GFP). In some embodiments, the labels may include, but are not limited to, fluorescent lanthanide complexes, including those of Europium and Terbium, fluorescamine, rhodamine, tetramethylrhodamine, eosin, erythrosin, coumarin, methyl-coumarins, pyrene, Malacite green, stilbene, Lucifer Yellow, Cascade Blue™, Texas Red, 1,1'-[1,3-propanediylbis[(dimethylimino-3,1-propanediyl]]bis[4-[(3-methyl-2(3H)-benzoxazolylidene)methyl]]-,tetraioide, which is sold under the name YOYO-1, Cy and Alexa dyes, and others described in the 9th Edition of the Molecular Probes Handbook by Richard P. Haugland, hereby expressly incorporated by reference.

In one embodiment the kit comprises the device or device array of this invention further comprises a chemical or a biological reactor. In one embodiment, before a particle stream enters the device or after particle stream exit the device, particles undergo a chemical or a biological reaction in the coupled reactor. In one embodiment prior to passage through the device, the particles are purified, filtered or rinsed.

In one embodiment the apparatuses/devices/kits of this invention comprise/accommodate incorporation of reagents to promote adhesion of the cells to specific chambers of the capture units as herein described. In some embodiments, the In one embodiment the apparatuses/devices/kits of this invention comprise/accommodate incorporation of reagents to diminish adhesion of the cells to specific chambers of the capture units as herein described. In some embodiments, the apparatuses/devices/kits of this invention comprise/accommodate incorporation of reagents to dislodge cells which have adhered to a surface of the device, for example, in the chamber, or between chambers of the device. Such reagents are well known in the art, and may comprise, for example, enzymes or detergents, for example, triton-X, saponin, trypsin, and others known in the art.

In some embodiments, the devices of this invention are so constructed to be of modular design, such that multiple patterning devices may be inter-connected to each other, and/or to other modules, such as those for mixing, analysis, imaging, etc., and yet contained within a single housing, in one embodiment. In another embodiment, the design construction is such that numerous arrays can be so constructed, such that any combination of connections may be achieved at a given time. In some embodiments, a plurality of patterning devices are provided within a single housing along with a plurality of sources for inducing flow and means for detection and/or analysis. In some embodiments, the individual modules can be replaced without removing or exchanging the remaining modules. Dovetail rails and other mechanical assemblies facilitate the swapping of modules in and out, in some embodiments.

In some embodiments the invention provides a kit of parts, for example a kit comprising the first substrate and capture units. According to this aspect and in some embodiments, the second substrate may be provided separately. In some embodiments, the device is constructed so as to be readily compatible for use with existing cell analysis or culture materials, such as 96 well plates or covers, coverglasses or microscope slides, flexible covers, aluminum foil cover, or plastic wraps. In some embodiments a kit comprising two or more substrates with capture units is provided with a means to attach them together. In some embodiment the substrates containing the capture units are sandwiched together. In some embodiments, for larger scale capture units, the capture units are provided unattached to a first substrate so that they can be subsequently positioned, spread, glued, adhered, bonded, pressed between additional substrates or the walls, bottom or top of existing kits or units. Such kits or units comprise microfluidic devices, 96 well plates, cell culture plates, tissue culture scaffolds or sample holders suitable for a microscope stage, for focused spectroscopy, and for microfluidic devices connected to analysis tools, such as cell cytometers, fluorescent imaging, chromatography and separation devices, and chemical analytical instruments such as mass spectra, NMR, HPLC, GC, Electroanalytical devices, or surface imaging techniques. In some embodiments where a kit of the present invention is supplied without one or two substrates, the substrates can be later attached using caulking or filler material placed around the sides of the two substrates. The microfluidic device can be sealed by applying rubber, glue, plastics, silica sealers to the sides of the two substrates comprising the device. The device, when supplied with a first substrate comprises the capture units, contain in some embodiments a wall all around the substrate made out of PDMS or compatible materials that will be attached to a second substrate yet leaves a space between the capture units and the second device to accommodate fluid flow.

IV. Methods of Use of the Particle Capture and Pair Devices of the Invention

In one embodiment, the invention provides for a method of particle capture and/or pairing, the method comprising applying liquids comprising the particles of interest to a device of this invention.

In one embodiment, this invention provides a method for patterning individual particles, said method comprising:
(i) applying a first liquid comprising a series of first particles to a particle patterning device under flow in a first direction, whereby an individual particle is accommodated within a first chamber in a first capture unit of said particle patterning device, said device comprising:
    a first substrate;
    at least one capture unit positioned such that the top of said capture unit is adhered to or contiguous with said first substrate, said capture unit comprising:
        a first chamber comprising at least one opening, sized to trap and accommodate a single particle; and
        a second chamber comprising at least one opening, sized to trap and accommodate a single or more than a single particle;
    wherein an opening of said first chamber faces a direction opposite to that of an opening of said second chamber, and said opening of said first chamber is contiguous with a side of said capture unit, said opening of said second chamber is contiguous with an opposite side of said capture unit;
    optionally a second substrate positioned proximally to or adhered to a bottom of said capture unit or a portion thereof;
    a conduit through which first flow may be induced in said device, such that fluid flow is accommodated at least between said capture unit and said second substrate and particles positioned within said first or second chamber are subject to said fluid flow; and
    optionally, a second conduit through which a second flow may be induced in a direction opposite to that of said first flow; and
(ii) applying a second liquid to said device under flow in a second direction, wherein said individual particle moves from said first chamber of said first capture unit to a second chamber in a second capture unit.

In one embodiment the method further comprising the step of applying a third liquid comprising a series of second particles to said device under flow in said second direction, whereby the series of second particles are patterned in the second chamber in the second capture units with the series of first particles. In one embodiment, there is a contact between two particles patterned in the same chamber.

In one embodiment, the method further comprises the step of applying a third liquid to said device under flow in said first direction, whereby said individual particle moves back to said first chamber in said first capture unit.

In one embodiment, the liquid comprises a suspension of particles, or in another embodiment, a cell or tissue homogenate, or in another embodiment, a culture supernatant, or in another embodiment, a culture, or in another embodiment, a biological fluid, or any sample with appropriately sized particles whose capture is desired.

In one embodiment the liquid is aqueous. In one embodiment the liquid is organic. In one embodiment the suspension contains inorganic microparticles or nanoparticles.

In one embodiment, the particles of interest comprise cells, including prokaryotic or eukaryotic cells, organelles, viral particles, beads, microparticles, vesicles, liposomes, nanoparticles or combinations thereof.

In one embodiment the method further comprises the manipulation of the environment of trapped particle 1/particle 2 pairs.

In one embodiment the manipulation is carried out by introducing chemicals through the liquid. In one embodiment the manipulation involves the introduction of a marker. In one embodiment manipulation involves chemicals that can induce cell fusion. In one embodiment chemicals that can induce cell fusion are membrane-permeable. In one embodiment the manipulation involves pH change in the liquid. In some embodiment manipulation involve introduction of salts into the liquid. In one embodiment the manipulation involves changing the concentrations of salts, or changing the solution. In one embodiment changing the concentration of solutes in the solution changes the osmotic pressure exerted on the cells. In one embodiment a change in the osmotic pressure, rupture the cell/vesicle and induce a chemical reaction between two cells in contact or between the contents of the cells/vesicles. In one embodiment changing the solution content, causes a chemical reaction on the surface of the trapped cells or particles. In one embodiment molecules are introduced into the devices of the invention. In some embodiments the biological molecules are proteins, DNA or lipids. In some embodiments the molecules bind or adhere to the trapped cells/particles.

In one embodiment manipulation involves changes in temperature of the solution. In one embodiment manipulation of the trapped particles involves binding of a fluorescent molecule to the cells from solution. In one embodiment manipulating the particles involves exciting a fluorescent molecule on or in the particles. In one embodiment the fluorescent marker is used to track trapping of particles. According to this aspect, and in one embodiment, the tagged bead is loaded and its deposition in an array comparable to that of the capture units confirms trapping of the particles, under flow. In one embodiment, a second suspension comprising for example, microscopic fluorescent-tagged particles is introduced to a device comprising tagged fluorescent beads with different excitation than that of the particles, and the beads are functionalized to specifically interact with the particles. In some embodiments, FRET is utilized to determine binding of the tagged particle with the bead, or colocalization of signals, etc., or in some embodiments, a reaction creating a particulate product may be evaluated by spectrophotometry, or others, as will be appreciated by the skilled artisan.

In one embodiment fluorescent markers are used to study the dynamics of particle trapping and reactions or fusion between particles. Similar to the methods described for trapping above, reactions or fusion between particles may be accomplished by observing changes in fluorescence, conductance, or other properties known to the skilled artisan, which reflect upon the proximal localization or contact between the captured particles in a series.

In one embodiment manipulation involves the introduction of nanoparticles to the solution. In one embodiment the nanoparticles are fluorescent. In some embodiment the nanoparticles comprises a coating that permits binding of nanoparticles to other particles or cells.

In one embodiment optical manipulation is carried out on the trapped particle or trapped particle pairs. In one embodiment optical manipulation causes a chemical reaction involving the materials of the two or one of the particles. In one embodiment optical manipulation causes polymerization of material in or at the surface of particles 1 or 2 or a combination thereof. In one embodiment optical manipulation changes the contents or function of the cell. In one embodiment optical manipulation changes the membrane of the cell. In some embodiment optical manipulation induces cell fusion. In some embodiment optical manipulation extract a particle pair from the capture unit. In some embodiment optical manipulation extracts only particle 2 from the capture unit.

In one embodiment the method further comprises electrical manipulation of the particle pair. In one embodiment microelectrodes located within or around or at the vicinity of the large capture unit can generate an electric field. In one embodiment the electric field can induce membrane permeability. In one embodiment said membrane permeability of cells 1 and cells 2 results in the exchange of intracellular material between cell 1 and cell 2. In some embodiments said electrical manipulation causes cell fusion. In some embodiments electrical manipulation enhances or reduces the adherence of cells to the capture unit. In some embodiments electrical manipulation alters the functionality of a cell. In some embodiment electrical manipulation involves the application of a voltage on a pair of conducting or semiconducting or a combination of conducting and semiconducting microparticles. Such application results in measurable changes in conductance, which may be detected by multiple standard means known in the art.

In some embodiments said application of voltage results in light emission. This, as well may be detected by known means, for example with the aid of a luminometer.

In some embodiments said application of voltage results in an electrical current flow. In one embodiment electrical current raises the temperature of the two particles. In some embodiments one or more particles reaches their melting point. In some embodiments electrical current cause the deformation of one or both of the microparticles. In one embodiment said current induces fusion of two microparticles. In one embodiment said fusion results in a larger single microparticle. In another embodiment fusion results in a metal alloyed particle, and in yet another embodiment fusion results in a core-shell particle. In one embodiment the result of said fusion and or said melting is a particle assuming the U-shape or any other shape of the chamber. In another embodiment the result is a spherical particle. In one embodiment the controlled capture of metallic and/or semiconductor particles between microelectrodes is used to construct molecular electronics devices and devices for quantum computing.

In one embodiment the method further comprises the observation of the trapped particle pairs. In one embodiment such observation involves microscopy. In some embodiments said microscopy is optical. In some embodiments said microscopy is conducted before, during and after particle pairing. In some embodiments said optical microscopy involves a white light source an in other embodiments a laser light source. In one embodiment an optical micrograph of a large part of the array containing many capture units is taken. In one embodiment a real time movie can be made using said microscopy before, during and after particle capture-and-pair and before-during and after particle manipulation in the capture unit. In one embodiment microscopy is electron microscopy. In one embodiment microscopy is scanning electron microscopy (SEM). In one embodiment an SEM image of a large part of the array containing many capture units is taken. In one embodiment a close-up SEM image shows the result of particle pair manipulation within one capture unit. In one embodiment observation is automated and capture units are observed serially. In one embodiment serial observation is carried out using microscopy. In one embodiment the device is attached to a computerized moving stage. In one embodiment observation is followed by serial analysis of the capture units. In one embodiment statistical analysis is carried out for an array of capture units. In one embodiment result of analysis is part of an algorithm that controls subsequent steps of processing or reaction or analysis. In one embodiment observation involves the use of an atomic force microscope (AFM). In one embodiment the second substrate used for sealing the device is removed and an AFM tip is directed to a capture unit. In one embodiment AFM is conducted in solution. In another embodiment AFM is conducted under ambient conditions or in vacuum. In one embodiment AFM is conducted at low temperatures. In one embodiment AFM images resolve the area of contact of the two particles. In one embodiment AFM images show a fused particle which is a product of a pair of particles undergoing a process.

In one embodiment a method of this invention further comprises collecting particles or particle pairs. In one embodiment collecting comprises the extraction of particles from the capture units. In one embodiment extraction involves the reversal of the flow direction such that a particle or a particle pair is extracted from the capture units by the flow. In one embodiment the extraction involves the application or removal of an electric field around the capture units holding the particle or particle pairs. In one embodiment said extraction involves an optical pulse or the introduction of a chemical from solution in order to extract particles from cells. For disposable devices, particle pairs or resulting particles are extracted by dissolving the PDMS matrix in a solvent. Particle collection, in one embodiment, comprises the attachment of a capture unit to one or two of the input/output ports. In one embodiment the input/output ports are connected to a flow cytometer for further analysis. In one embodiment said ports are connected to a test tube, a syringe, a vial, or an additional microfluidic device. In one embodiment the input/output ports are connected to a chemical reaction capture unit for further synthesis or analysis. In some embodiments said ports are connected to an evaporator for solvent evaporation. In some embodiments the particles are collected on a surface. In one embodiment said surface is a transmission electron microscope grid.

In one embodiment the method comprises the capture-and-pair of two particles of the same size. In one embodiment the particles are of different sizes. In one embodiment both particles are biological cells. In one embodiment one particle is a cell and one particle is a vesicle. In one embodiment one particle is a cell and one particle is a non-biological microparticle. In one embodiment the two particles are vesicles (liposomes). In one embodiment one particle is a liposome and one particle is a non-biological microparticle. In one embodiment the two particles are non-biological. In one embodiment at least one particle is metallic or semiconductor, or a salt or an inorganic particle, uncoated or coated by an organic layer. In one embodiment at least one particle is a polymer. In one embodiment a particle material is silica, glass, polystyrene, gold, CdSe or metal oxide. In one embodiment particles are core-shell particles. In one embodiment the core material is one and the shell material is another. In one embodiment core-shell particles have unique optical absorption and scattering properties. In one embodiment electrical properties of core-shell particles can be controlled. In one embodiment density of core-shell particles is designed. In one embodiment shell material is chosen such that it will bind biological or chemical functions. In one embodiment the particle surface comprises fluorescent markers. In one embodiment the particle itself is fluorescent.

In one embodiment the particle size ranges from between 1-10 nm. In one embodiment the particle size ranges between 10-100 nm. In one embodiment the particle size ranges between 100-1000 nm. In one embodiment the particle size ranges between 1-0.1-10 µm. In one embodiment the particle size ranges between 1-10 µm. In one embodiment the particle size ranges between 10-100 µm. In one embodiment the particle size ranges between 100-1000 µm. In one embodiment the particle size ranges between 20-70 µm.

In one embodiment two types of cells are paired by a method of this invention. In one aspect of this embodiment cells type 1 are trapped in the first chamber such that each cell is individually trapped in a different chamber. Cells type 1 are transferred into second chambers upon flow reversal and the introduction of a cell-free liquid. The geometry of the device in this aspect of the invention, allows only one cell to be trapped in each second chamber. Cells type 2 are introduced into the device with a flow direction that permits the trapping of one cell type 2 in each second chamber already occupied by one cell type 1. The dimensions of the second chambers are designed to fit two cells and therefore any additional cell trying to enter a two-cell occupied second chamber, will slide off the filled chamber and continue down the stream line. Two cells are paired in each second chamber and in one embodiment are held in tight membrane contact. In one embodiment the two cells are held in loose membrane contact.

In one embodiment a method of this invention comprises a MEM based device. In this embodiment a capture unit can rotate on an axis perpendicular to the fluid flow. Rotation of the capture unit is achieved using a micro-electro-mechanical switch incorporated with each capture units. The supporting pillars are designed such that rotation on the capture units is enabled. In one embodiment a method for capture-and-pair based on a MEM device comprises:

i. Orienting the capture units using the electro-mechanical switch such that the first chamber opening faces the fluid flow
 ii. Capture particles type 1 in the first chamber;
 iii. Rotating the capture units using the electromechanical switch such that the second chamber opening is now facing the fluid flow.
 iv. Transferring particles type 1 from first chamber to second chamber. Transfer is assisted by fluid flow.
 v. Introducing particles type 2 into the solution and capturing particles type 2 in same second chamber already occupied by particles type 1.

In one embodiment the MEM device is connected to a microscope and an algorithm is used for an automated process. In one embodiment the computerized microscope counts the number of filled capture units in step ii, and when the number exceeds a threshold, the MEM switch is activated to start step iii. In one embodiment the computerized imaging system counts the particles trapped in the large capture units in step iv, and if the number exceeds a threshold, an automated introduction of particles type 2 is activated for step v.

In one embodiment the invention provides a method for binding of non-biological particles to biological cells. In one embodiment the method comprises the steps of:

vi. capturing a biological cell in a large chamber;
 vii. capturing a non-biological particle in the same large chamber such that non-biological particle is held in tight contact with the membrane of the biological cell.

In one embodiment of this method the non-biological particle chemically binds the biological cell. In one embodiment the non-biological particle is coated with a material that enhances biological cell binding. In one embodiment the non-biological cell is coated with a fluorescent marker. In one embodiment the non-biological particle serves as a curved cell-growth surface for the growth of the biological cell. In one embodiment the non-biological particle serves as a load or a weight. In one embodiment the non-biological particle is made of a material such that it can be trapped using optical tweezers. In one embodiment said optical trapping of the particle enable the transfer of the biological cell to desired locations. In one embodiment the non-biological particle is made of a material which can be locally heated using a light source.

In other embodiments, various applications of the methods of the present invention are possible without deviating from the present invention.

By way of example, the capture-and-pair methods of the present invention allow for high-throughput robotic assaying systems to directly interface with the devices of the present invention, and to pair particles of interest, and/or to carry out two-particle processes.

In one embodiment, this invention provides a method of contacting individual particles, said method comprising:
 (i) applying a first liquid comprising a series of first particles to a particle patterning device under flow in a first direction, whereby an individual particle is accommodated within a first capture unit of said particle patterning device, said device comprising:
  a first substrate;
  at least one capture unit positioned such that the top of said capture unit is adhered to or contiguous with said first substrate, said capture unit comprising:
   a first chamber comprising at least one opening, sized to trap and accommodate a single particle; and
   a second chamber comprising at least one opening, sized to trap and accommodate a single or more than a single particle;
  wherein an opening of said first chamber faces a direction opposite to that of an opening of said second chamber, and said opening of said first chamber corresponds to a side of said capture unit, said opening of said second chamber corresponds to an opposite side of said capture unit;
  optionally a second substrate positioned proximally to or adhered to a bottom of said capture unit or a portion thereof;
  a conduit through which first flow may be induced in said device, such that fluid flow is accommodated at least between said capture unit and said second substrate and particles positioned within said first or second chamber are subject to said fluid flow; and
  optionally, a second conduit through which a second flow may be induced in a direction opposite to that of said first flow; and
 (ii) applying flow in a second direction, wherein said individual particle moves from said first chamber of said first capture unit to a second chamber in a second capture unit; and
 (iii) applying a second liquid comprising a series of second particles to said device in said second direction,
  whereby said second particles positioned within said second chamber are brought into contact with said series of first particles, thereby being a method of contacting individual particles.

In one embodiment, step (ii) may comprise applying an additional liquid in an opposing direction, to move the particle from the first chamber to the second chamber. In some embodiments, the additional liquid may comprise a reagent, which alters, reacts with or binds the first series of particles. In some embodiments, the additional liquid may comprise a solvent alone, or a solution, and in some embodiments, does not comprise any particles. In some embodiments, the method further comprises iterative introductions of liquids, including liquids comprising a compound or particle of interest to the device, which interacts with particles in the second chamber or deposits material within the second chamber, and optionally results in some change in the particles trapped/deposited within the second chamber.

In one embodiment, bringing the first and second series of particles into contact results in a transfer of materials from one particle to another. In one embodiment, the materials comprise a biological material, which in one embodiment is a nucleic acid or polypeptide.

In one embodiment, the particle is a cell, and in another embodiment, the method results in genetic transformation of said cell. For example, and in one embodiment, the first particle is a mammalian cell and the second particle is a virus, or comprises naked nucleic acid, or a plasmid, or a vector. According to this aspect, and in one embodiment, reagents may be introduced to facilitate transformation, known in the art, or electroporation may be accomplished, etc. In some embodiments, both particles may comprise bacteria, and the method may comprise a method of bacterial conjugation. In some embodiments, phage display may be accomplished using such methods, as well. In one embodiment methods of this invention enhance transduction efficiency.

In one embodiment, the first or second series of particles or a combination thereof are cells, and in one embodiment, the method comprises a method of cell fusion. For example, and in some embodiments, early events in bacterial invasion of a cell may be observed via the methods described herein. In some embodiments, cell fractions may be applied to methods of fusion, whereby for example, a phagosome comprising a pathogen is isolated from infected cells, and applied to a first chamber of a device, with the chamber sized to accommodate, for example, two organelles or two cells, such that subsequent application of fractionated vesicles from the infected cells are applied as well, under flow. Following this, a second flow in an opposite orientation is applied, removing the contents of the first chambers. Such contents may be allowed to remain outside a chamber for a period of time and under conditions allowing fusion events to occur. According to this aspect, and in one embodiment, the second chambers are oriented perpendicularly from the first chambers, and flow is now applied in a direction such that the contents of the first chambers are conveyed to the second chambers. Fused vesicles will transport as a single entity to the second chambers, whereas non-fused will remain separate, thus vesicular fusion with phagosomes may also be ascertained.

In one embodiment, the method comprises a method of single cell infection. For example, and in some embodiments, certain bacterial species are difficult to separate to single cell preparations, without the use of detergents, sonication, etc., which in turn may affect the bacteria. In some embodiments, applying a suspension of the bacteria under flow, wherein the chambers are so constructed so as to only accommodate single bacterial cells allows a means to isolate single bacteria without much bacterial manipulation, and subsequent infection of for example mammalian cells with the single pathogen may then be accomplished.

In another embodiment, the method comprises a method of phagocytosis. According to this aspect, and in some embodiments, early events in pathogenesis occur within seconds or fractions thereof of phagocytosis, which may be readily observed using the methods of this invention. In some embodiments, molecular interactions may be probed using the methods of this invention, as well.

In one embodiment a method of this invention is applicable to reprogramming of somatic cells through fusion with embryonic stem cells. In one embodiment a method of this invention is applicable to the generation of antibodies through fusion of lymphocytes and myeloma cells. According to this aspect and in one embodiment the method is applicable to hybridoma technology. In one embodiment this method provides for high yield hybridoma technology. In one embodiment the method provides a tool for comparing fusion events in a diverse population of cells.

In one embodiment the device and methods of this invention enables fusion of cells. In one embodiment fusion is chemical. In one embodiment fusion is initiated by flowing polyethylene glycol (PEG) or other chemical fusion agent past the cells. In one embodiment the chemical fusion agent is subsequently replaced with a media. In one embodiment chemical fusion is performed with commercially available fusion buffers.

In one embodiment fusion is electrical. In one embodiment electrofusion is initiated by applying an electric field across the capture area. In one embodiment the electric field is applied by extending wires into reservoirs at either end of the device. In one embodiment the electric field is applied by plasma bonding the PDMS device to a glass slide with pre-patterned metal electrodes. In one embodiment each chamber is individually electrically addressed. In one embodiment short pulses are applied to fuse the cells in the presence of a fusion buffer, and then the cells are washed in media. In one embodiment, the device can interface with commercially available electrofusion power supplies.

In one embodiment the device and methods of this invention provide advantages over existing methods. In one embodiment current fusion protocols bring the cells together either through pelleting the cells or by applying an AC field to polarize the cells. Though the cell membranes are in contact there is no specificity in such methods in how the cells are paired. As a result, the fusion yield is low and can range around ~1 to 8%. In one embodiment fusion yield refers to the number of desired fusions as compared with the background of improperly fused and unfused cells. In one embodiment, using the device and methods of the present invention, the majority of the cells are properly paired through the loading process, leading to a high fusion efficiency. In one embodiment this allows the entire cell population to be used for pooled population assays.

In one embodiment the device and methods of this invention provides immobilization of cells during and after fusion processes. In one embodiment the cells are paired into a regular array and are packed closely together, allowing observation of thousands of cell pairs under a microscope. During the entire fusion process, in one embodiment, the cells remain immobilized. In one embodiment, membrane reorganization and exchange of cell contents can easily be observed for thousands of cell pairs in parallel. In one embodiment, the cells remain immobilized after the fusion process, and can remain immobilized for an indefinite length of time. In one embodiment this is in contrast to current commercial bulk protocols that can deliver large numbers of cells, but does not allow observation of the cells during the process.

In one embodiment this invention provides new fusion protocols. In one embodiment, the cells are immobilized in a microfluidic device of this invention and fusion buffers are flowed past them. In one embodiment the environment around the cells can be quickly changed. In one embodiment the environment around the cells can be quickly in about 1 minute. In one embodiment the environment around the cells is changed simply by changing the solution at the inlet of the device or at the inlet of a reservoir. In one embodiment, as a result, chemical and electrical fusion can be combined by switching the fusion buffers while the cells remain immobilized and properly paired. In one embodiment multiple doses of fusion protocols can be applied without losing cell contact, increasing the overall fusion efficiencies.

In one embodiment devices and methods of this invention can be optimized for fusion applications. In one embodiment the PDMS chambers, capture units, capture unit arrays or a combination thereof can be put into devices with many different geometries, such as parallel reaction compartments to test different fusion protocols. In one embodiment, one such example is an optimization device to determine the best fusion potentials. In one embodiment, a device with four parallel compartments, each containing an array of capture units is plasma bonded to a glass slide with electrodes of different gaps. In one embodiment, with the application of one voltage, four different electric fields are applied across the four different compartments. In one embodiment, the number of parallel compartments is flexible. In one embodiment the size of the gaps between the electrodes can be easily varied. In one embodiment such flexibility and variability allows coarse or fine optimization over numerous parallel compartments.

In one embodiment, the device interfaces with commercially available chemical and electrical fusion technologies. In one embodiment the device provides a new method of capturing and pairing the cells prior to the application of the fusion pulse or the fusion trigger. In one embodiment, the process of fusion can be monitored. In one embodiment a large number of successfully fused cells can be supplied. In one embodiment the device can eliminate the need for days of culturing and colony picking to isolate the desired fusion events. In one embodiment such elimination reduces both the time and consumables required to create a new fusion cell line.

In one embodiment, bringing the first and second series of particles into contact results in a measurable energy transfer, which in one embodiment is fluorescent resonance energy transfer (FRET), as described and as will be appreciated by one skilled in the art.

In another embodiment, the method comprises a screen for molecular interactions. As noted herein, the method may comprise patterning a first particle or cell in a capture unit, allowing a subsequent assay or interaction to proceed, removing the cell and transferring it to another chamber such that for example, it is possible to detect binding or fusion events, thereby screening for agents which promote or interfere with the same. In another embodiment, removing the cell following previous exposure to a reagent or assay may result in changes in the cells phenotype or activity, which in turn may be measured, and serve as a screen for effects of the agent applied thereto in this regard.

It will be appreciated that any time of reaction or interaction between two particles or two materials adhered to particles may thus be assayed, screened or ascertained and represents an embodiment of the invention. Such methods may be particularly useful in high-throughput assays and screens, for example, in screens for activity of certain agents, such as antiviral drugs, assayed for their ability to prevent for example, syncitia formation in HIV-infected lymphocytes, or many other applications, as will be appreciated by the skilled artisan.

In one embodiment, this invention provides controlling for cell contact and pairing in a microfluidic device. In one embodiment, the efficiency of different fusion impulses was evaluated based on independent measurements of fluorescence exchange and membrane reorganization. In one embodiment, the efficiency of generating fused cells with our device was compared with that using conventional protocols. In one embodiment, in devices of the present invention, electrofusion resulted in higher fusion efficiencies than chemical fusion likely because of the tight membrane contact between cell pairs when fused in the cell trap. Although we observed higher fusion efficiencies with electrofusion, this may change for cell pairs of widely divergent sizes. As the threshold voltage for generating pores required for electrofusion depends on cell size, and applying too much voltage across the membrane can cause cell lysis, two cells of very different sizes may be difficult to electrofuse successfully. In this case, fusion using PEG may be superior in one embodiment.

Considering that fusion efficiency depends on both pairing and initiation of fusion, and electrofusion yields in our device were up to ~90% in one embodiment, it is clear that pairing represents the crucial step for high-yield generation of properly fused cells. The 70% pairing efficiency that was achieved in some embodiments, is a substantial improvement over the 25% pairing efficiency previously reported for biotin-streptavidin-linked cells. In one embodiment, processes of the present invention are advantageous as they do not require cell-surface modification. Also, the 51%±16% fusion efficiency for 3T3s obtained in some embodiments, represents a fivefold increase over the control and previously reported microfluidic fusion yields.

In one embodiment, cytoplasmic exchange for thousands of fusion events in parallel was analyzed, and a slower mode of membrane reorganization was observed in cells labeled with CellTracker dyes. For example, 25 min after fusion initiation, 24% of CellTracker-labeled 3T3 fibroblasts had reorganized membranes versus 91% of eGFP-DsRed-expressing 3T3 fibroblasts according to one embodiment. Close inspection indicated that for many CellTracker-labeled cells the fluorescence was still somewhat partitioned, and the membrane reorganization, though initiated, was not completed within the same time frame as for as eGFP-DsRed-expressing cells.

In one embodiment, devices of this invention provided insight into the fusion process, allowing to decouple fluorescence exchange and membrane reorganization and to compare PEG and electric fusion. In one embodiment, devices of this invention can be used for on-chip analysis of a variety of fusion-based studies between two-color, one-color and even unstained cells. Cells fused in devices of the present invention maintained their viability and morphology off-chip. When mEFs were fused to mESCs in a microfluidic device of this invention and plated into a tissue culture dish, reprogramming of mEFs was observed. Because devices of this invention can maintain cell registration and analysis in the array, its use to characterize fusion-mediated reprogramming of somatic cells is anticipated in one embodiment.

Various modes of carrying out the invention are contemplated as being within the scope of the following claims particularly pointing out and distinctly claiming the subject matter, which is regarded as the invention.

EXAMPLES

Methods

Microfluidic Device Fabrication and Setup.

Masters for the microfluidic device were made from SU8 (MicroChem) spun on silicon wafers using standard photolithographic techniques. PDMS was poured over the master and then degassed before curing. Glass slides with electrodes were constructed from mask blanks precoated with chrome and photoresist (Telic), patterned by a transparency mask exposed to UV light. The PDMS devices and glass slides were assembled using plasma bonding. The devices were blocked with 7.5% bovine serum albumin and rinsed with phosphate-buffered saline (PBS) before use. Cells were manually placed in the top inlet reservoir and drawn through the device at 15-50 mms-1 using a syringe pump.

PEG Fusion in the Microfluidic Device.

$5\times10^5$ cells of each cell type were pelleted and resuspended in ~500 ml of medium. The suspension was filtered through a 35 mm cell strainer (BD Falcon) and loaded into the device as described previously. All solutions and media were kept at 37° C. PEG-1500 was put into the inlet reservoir and drawn past the cells at 0.4 µl/min for 3-5 min. The cells were washed with 1:1 PEG:medium for 1 min, then incubated in medium for 26 min. At time (t)=30 min, the cells were washed with trypan blue (10% in PBS; pH 7.4) for 5 min, then with medium for 5 min. At t=40 min, the second dose of PEG was applied, and the entire protocol was repeated for a total of 4 doses.

Electrofusion in the Microfluidic Device.

The electrodes for electrofusion were connected to a power supply (Eppendorf) in parallel with a 50 kΩ resistor. After cell loading, the device was flushed with hypoosmolar fusion buffer at 0.4 µl/min for 10 min. The cells were pulsed at varying voltages (0.5 to 2.0 kV cm$^{-1}$) for 50 µs×5 pulses. Hypoosmolar fusion buffer was flushed past the cells for an additional 10 min before being replaced with warm medium. The cells were then incubated for an additional 15 min at 37° C.

Image Acquisition and Analysis.

The microfluidic device was placed on an automated inverted microscope (Zeiss Axiovert 200 m) fitted with a stage incubator (In vivo Scientific) and images were acquired either every 2.5 min or 5 min. A single randomly chosen image field (~200-300 capture combs) was used for each experiment, and the size of the image field remained constant. Images were analyzed in ImageJ (US National Institutes of Health) to determine pairing efficiencies (number of traps in the field of view occupied with a single cell of one type in the bottom of the well with a second cell (or more) of the other type on top) and fusion efficiencies (based on fluorescence exchange or membrane reorganization). Fluorescence exchange efficiencies were also analyzed using an automated macro written in ImageJ.

Example 1

An Embodiment of a Capture-Comb Device of this Invention

Figure 1:
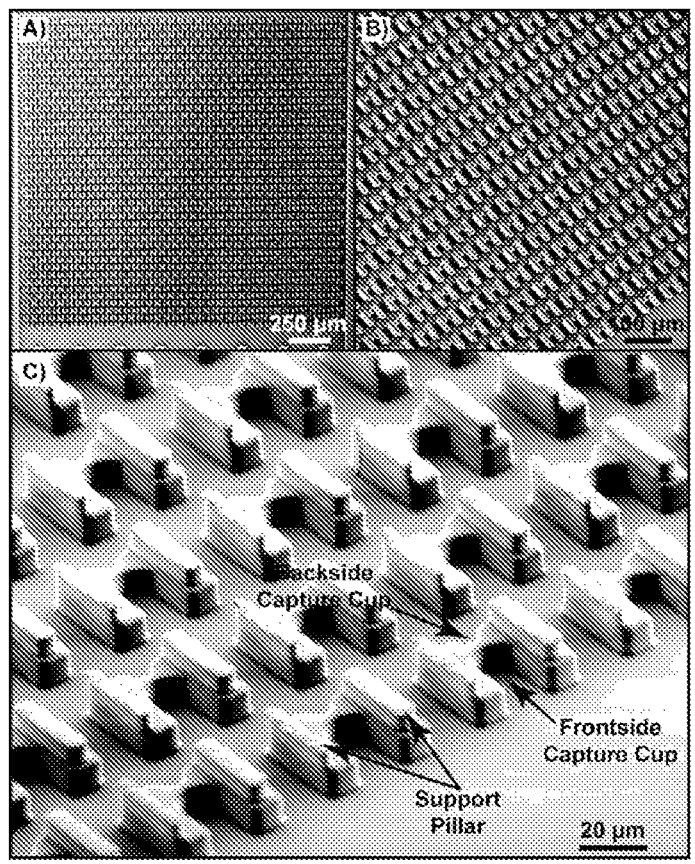
FIG. 1 schematically depicts an embodiment of a device of this invention. SEM images of the capture device are shown. Each capture unit consists of front and back chambers. Support pillars maintain proper spacing of the chambers from the surface of the second substrate.

An embodiment of a device of this invention, comprising a two-cell Capture and pair device was fabricated as part of a microfluidic system (FIG. 1). The capture-and pair device comprised a microfluidic chamber with an array of capture units, each capture unit holding two chambers. The two chambers were positioned back to back within each capture unit. The opening of the two chambers were oriented in and against the direction of a fluid flow, respectively (see FIGS. 1 and 2). The two chambers in each capture unit differed in size.

Figure 2:
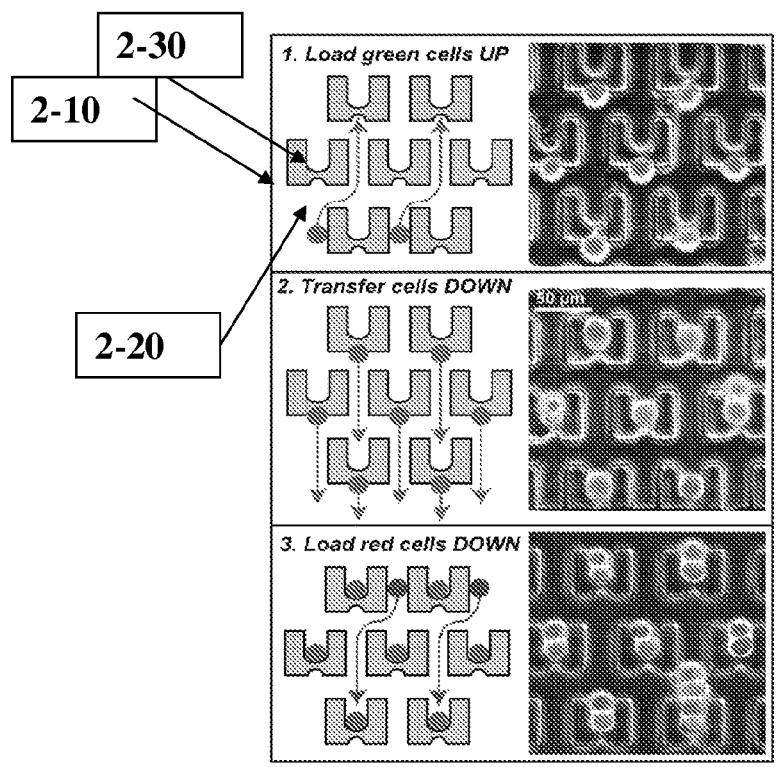
FIG. 2 schematically depicts an embodiment of a method of this invention. A schematic of a two-cell loading process is illustrated on the left. On the right, fluorescent microscopy images are shown for the two-cell capturing and pairing process. Three steps are presented top to bottom: (1) Loading of cells type 1 in a direction where fluid flow opposes the opening of the first, smaller chambers, so cells from the fluid can be trapped in the first, smaller capture units; (2) Reversing of the fluid flow direction such that the cells type 1 exit the first, small capture units and enter the opposing second, larger capture units. (3) Introduction of cells type 2 with the same fluid direction, such that cells type 2 can enter the second, larger capture units and join cells type 1 (green) that are already trapped in it.

The elements of an embodiment of this device are schematically depicted in FIG. 2. According to this aspect, 2 chambers (2-20; 2-30) are so positioned within the capture unit (2-10) such that openings of each chamber faces opposing directions. The first chamber has a smaller depth (2-20), while on an opposite face of the unit, the second chamber having a larger depth is positioned (2-30). The depths are constructed to accommodate capturing a desired material, for example, a single cell (2-40) is accommodated in the first, smaller depth chamber, whereas 2 or more cells may be accommodated in the second, larger chamber, within a capture unit. The first chamber, in this embodiment, has the dimensions of a single cell (e.g. 10 μm wide×5 μm deep×12 μm tall) while the second chamber has a depth that accommodates two cells (18 μm wide×25 μm deep×12 μm tall). Two input/output ports are connected to the array on opposite sides. Fluid flow (dotted arrows) is in a direction such that cells introduced in the device under flow are trapped within the first chambers of the capture units of the device, as a function of the flow being in the direction of the opening to the first chambers and opposite in direction to the opening of the second chambers.

According to this aspect and in one embodiment, a first type of cells are flowed into the device, wherein the flow direction is toward that of the opening of the first chamber with a smaller depth (panel A). Cells which are not captured therein are flowed out of the device, thus enabling single cell capture. The unit is so designed, such that the array of capture units is suspended on posts, such that cells trapped within capture units are still influenced by flow conditions. A second flow is applied in the opposite direction as that initially applied, and single trapped cells are now flowed out of the first, smaller chambers (FIG. 2B). The design of the device is such that a capture chamber having a larger depth has an opening which faces the direction of the second flow, such that the cells flowed from the smaller capture chambers are now delivered to the larger capture chambers (FIG. 2C). Any number of materials can be introduced under flow in this direction (FIG. 2C), to load additional materials in the chamber of larger dimensions (blue circles). For example, additional cells or particles, or particulate material may be loaded and deposited in the larger capture chamber, with a myriad of applications, as will be appreciated by one skilled in the art.

As a result, in this embodiment, the capture chamber of larger dimensions, will comprise a single cell (2-40) and a second deposited single cell or particle (2-50), held in tight membrane contact. Manipulation of the deposited material may be conducted, for example, by assay, electrical manipulation or optical techniques.

Since the capture-comb device is constructed of transparent material (Polydimethylsiloxane), the deposited material, e.g., cells, can be observed under a microscope.

In some embodiments, cell-to-cell fusion and exchange of intracellular material may be effected, and material deposited in the capture unit of larger dimensions may be released from the traps by reversing the direction of the flow.

Example 2

Capture and Pair of Two Different Cell Types

Figure 3:
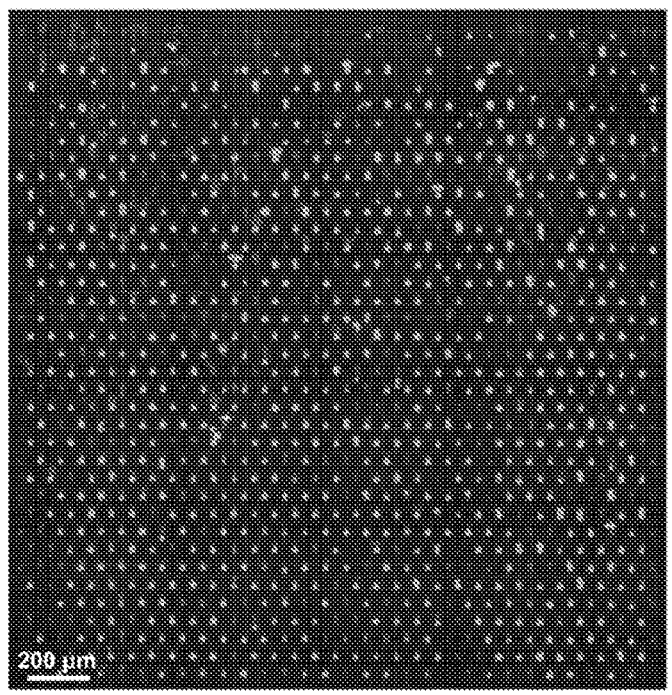
FIG. 3 is a fluorescent overlay image of one embodiment of the present invention. The image shows captured red (darker) and green (lighter) 3T3 cells. The cells were loaded sequentially as described in FIG. 2.

FIG. 2 (right panel) and FIG. 3 are fluorescent overlay images. Cells were applied to the device and captured in the chambers as described in Example 1, representing an embodiment of a method of the present invention. Red and green NIH 3T3 cells were loaded sequentially as described above. Cells were labeled with CellTracker® green and orange. In some embodiments 3T3s were used with stably-integrated GFP and RFP. In some embodiments GFP-positive mouse embryonic stem cells and Hoechst-stained mouse embryonic fibroblasts were used. In other embodiments, GFP-positive mouse B-cells and unstained myeloma cells were used.

Cells of a first type (green) were loaded in a direction where fluid flow was in a direction opposite to the openings of the first chambers in the capture device, thus cells were trapped in the first, smaller chambers. Fluid flow direction was then reversed such that the trapped cells within the first chamber were then flowed to opposing, second, larger chambers in the capture device. A second cell type was introduced in the device, in the reverse flow orientation such that cells of the second type entered the second capture units and joined cells type 1 that were already trapped in it.

Example 3

Two-cell Capture-Comb Device for Attaching Fluorescent Tags to Cells

A two-cell Capture-comb device as described in Example 1 is fabricated. A mixture of cells of a first type is loaded in the device and cells are transferred to capture units of larger dimensions as described in Example 1. Fluorescent beads or quantum dots are introduced into the device as described in FIG. 1C, whereby the beads or dots are introduced to the capture units of larger dimensions comprising the initially loaded cells. The dimensions of the capture units are constructed such that each capture unit can only hold one cell and one bead or quantum dot. The beads or quantum dots, in some embodiments, are functionalized, so that they specifically interact with the cells. Upon release of the cells from the device by reversing fluid flow, as described, released cells are conjugated to the beads or quantum dots.

Example 4

Two-cell Capture-Comb Device for Microsynthesis

A two-cell capture-comb device is constructed as described in Example 1. A mixture of vesicles of a first type is loaded in the device and transferred to the capture chambers of larger dimensions as described in Example 1. Each vesicle encapsulates a reagent or reagents. Vesicles of a second type are loaded, as well. The vesicles of the second type encapsulate a second reagent or reagents. Loading of the two types of vesicles, results in localization of both vesicle types in the large capture chamber, each encapsulating one or more reagents. Chemical, optical or electrical manipulation may be conducted, such that vesicular fusion occurs, and the intravesicular reagents from both vesicles are mixed. In some embodiments, mixing of the reagents from the two vesicles inside the new fused larger vesicle enables a chemical reaction. Upon release of the fused vesicles using reverse flow, a chemical product may be obtained, which is protected within the formed fused vesicle.

Example 5

An Embodiment of Use of the Two-Cell Capture-Comb Device for Cell Transformation Using Stem Cells The fabrication of a two-cell Capture-comb device is accomplished as described in Example 1. A mixture of a first stem cells type is loaded into the device and transferred into the larger capture chambers using the technique described in Example 1. Adult (somatic) cells are loaded and trapped in the large capture chambers, as described, thus adult cells and stem cells are paired in each chamber of the capture unit in tight membrane contact. Chemical or physical manipulation may cause the adult cells to de-differentiate back to an embryonic state, thus providing an environment for early tissue regeneration.

Example 6

MEM-based Two-cell Capture-Comb Device

A two-cell Capture-comb device is described wherein the chamber can rotate by applying an electrical force. The rotation of the capture unit flips the first and second capture chambers 180 degrees with respect to their original orientation. After cells are loaded, flipping of the chamber eliminates the need to change flow direction, which in some embodiments is a time-saving advantage. After chamber flipping, initially loaded cells or particles are transferred by to the second, larger capture chambers. Additional cells and/or particles may be introduced to the second, larger chamber, by introduction through the appropriate port.

Example 7

Exchanging Intracellular Material Using Electroporation

A two-cell Capture-comb device is constructed as described in Example 1, with the addition of equipping each unit with two microelectrodes. Once the desired number of cells or vesicles are trapped in the appropriate capture unit, an electric field is applied, which causes an increase in permeability of the cell or vesicular membranes. This permeability results in an exchange of intracellular material between the two cells, allows for introduction of genetic material, for example, or any desired substance, such as a drug or a molecular probe. Upon removal of the electric field, the transient cell membrane permeability declines.

Example 8

Controlled Release of Modified Cells Using Dielectrophoresis

A two-cell Capture-comb device is constructed as described in Example 1 and as described in Example 7. The microelectrodes leading to a capture unit can be individually addressed [for example as described in "A Scalable Addressable Positive-Dielectrophoretic Cell-Sorting Array" Brian M. Taff and Joel Voldman, Anal. Chem. 2005, 77, 7976-7983, incorporated fully herein by reference]. Once two cells are trapped, and the desired interaction between the cells accomplished, application or removal of an electric field for a specific capture unit causes release of the cell pair or of the resulting single cell from the capture unit. Fluid flow enables the collection of the released cells or particles.

Example 9

Microparticle Synthesis

Particles for use in the capture devices of this invention may comprise multiple materials. In some embodiments, particles comprised of one material are loaded first, according to methods described in Example 1, and particles comprised of a second material are subsequently loaded. In some embodiments, once the two particles are paired, the environmental conditions are changed. Such changes may include temperature, pH, solvent, solution composition, exchange of liquid flow with gas or a gaseous mixture flow, gas pressure etc. The changes induce a chemical reaction between the two particles. Depending upon the size and chemical composition of the particles a variety of products are obtained. For a pair of metallic particles for example, core-shell particles can be made if the temperature is elevated to the melting temperature of one particle keeping the other particle in the solid state. Under controlled conditions, the melted metal can coat the solid particle resulting in a core-shell bimetallic microparticle. The size of the core and the size of the shell can be precisely designed by choosing the original size of the two particles, or by choosing the size of the capture unit trap. A metal alloy can be similarly formed at a temperature where the two metals melt. The two metals will mix, and upon cooling a metal alloy will be formed. The chemical formula of the resulting alloy will be defined by the size of the original particles and by the synthesis conditions. The processes mentioned in this example can be observed in real time using a microscope. The processes mentioned in this example are not limited to metals and can be performed with any combination of materials.

Example 10

Microfluidic Control of Cell Pairing and Fusion

Microfluidic Device Design

Figure 5:
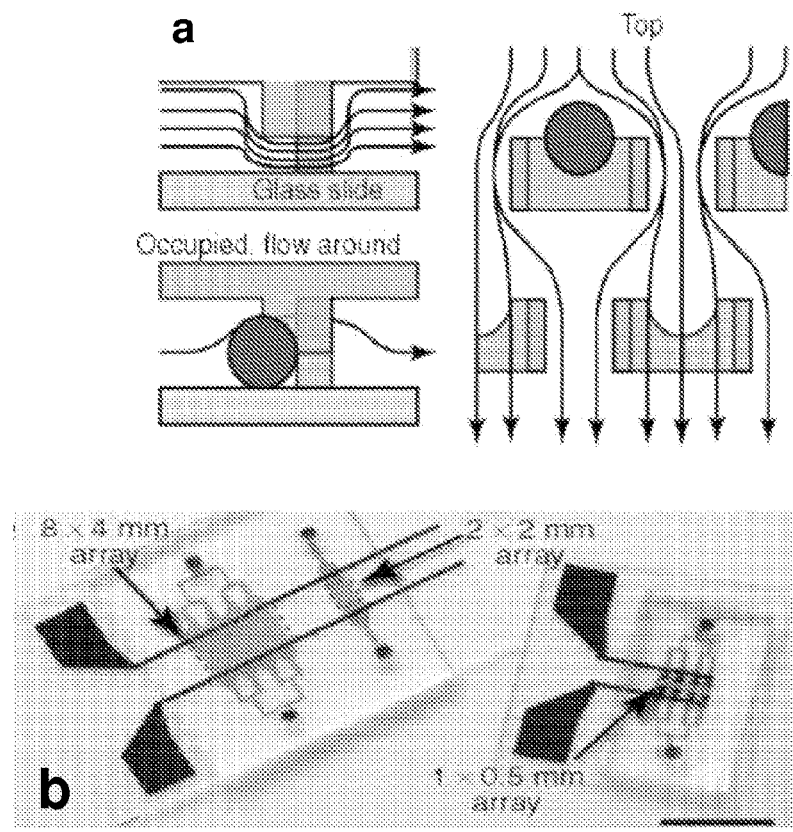
FIG. 5 illustrates embodiments of a microfluidic device for cell capture and pairing. (a) Schematic of the microfluidic device operation and structure. The flow passes under the cell trap, directing the cells into the capture cup. The support pillars maintain the proper vertical gap. (b) The 2×2 mm array is in a 1.8-cm-long channel and contains ~750-1,200 traps; the 8×4 mm array is in a 2.5-cm-long device and contains ~6,000 traps; and the 1-mm-wide×0.5-mm-long array (used primarily for optimization of trap geometry and fusion voltages) is in a 1.8-cm-long device array and contains ~100 traps per channel. Scale bar is 1 cm in (b).

The cell capture device comprised thousands of polydimethyl siloxane (PDMS) cell traps densely arrayed within a flow-through channel. Each cell trap consisted of a weir structure that extends vertically into the channel and contained front-side and back-side capture cups (FIGS. 1a-c and FIGS. 5a, b). Support pillars placed on either side of the capture cups allowed flow into and under the trap. The pillar heights were tailored to be slightly smaller than the cell diameter so the cells were trapped once they entered the capture cup. The support pillars also maintained proper channel height across the array once the device was bonded to a glass substrate. The cell traps were incorporated into three different devices; the largest was 8 mm×4 mm and contained ~6,000 traps (FIG. 1e5b). It was observed that the trap spacing within the array was critical for efficient capture without clogging. With optimal column spacing (~1-1.5 cell diameters, ~20 µm) and a row spacing of 20-50 µm, 70-90% of the cells that entered the array could be captured.

Cell Capture and Pairing 2-cell capture and pairing was accomplished using a three-step loading protocol. First, single cells were isolated in the smaller backside capture cup (FIG. 2(1)). Once the array was saturated, the cells were transferred directly 'down' into the opposing larger capture cup (FIG. 2(2)). This transfer was fast (<1 s), massively parallel and highly efficient because of the laminar flow within the device. Finally, the second cell population was loaded and trapped immediately in front of the previously trapped cells (FIG. 2(3)). The larger front-side cup was sized to trap 2 cells, so additional cells traveled through the array until it was saturated. The obtained 2-cell capture efficiencies were up to ~80% (percentage of traps occupied by exactly 2 cells of any type) and pairing efficiencies of up to 70% (FIG. 3).

Higher efficiencies were possible in the middle and bottom of the array where less penetration of larger cell clumps and therefore better single cell transfer occurred.

Fusion in the Microfluidic Device

The compatibility of the device with both chemical and electrical fusion protocols was tested. Fusion efficiencies were determined for all experiments by imaging and counting the number of cells that exchanged fluorescent molecules (indicative of initiation of fusion) and/or exhibited plasma membrane reorganization (indicative of advanced fusion).

First, the capability of the device to fuse different cell types using PEG was explored. PEG was flowed past the cells causing them to shrink from the osmotic shock. During this time, the cells remained in contact and stationary within the array, demonstrating that the trap geometry can successfully immobilize the cells even though there is a substantial change in cell volume. Next, the PEG was washed out with medium, causing the cells to swell back to their original size and initiate fusion. One advantage of the device is that solutions can be exchanged rapidly while the cells remain paired and in contact; therefore, additional doses of PEG can be applied to increase fusion efficiencies without losing cell pairing or registration. The effect of multiple PEG doses was determined on either unlabeled or CellTracker-labeled 3T3s paired in the device. A wash with a single dose of PEG yielded 15% fluorescence exchange over CellTracker-labeled 3T3 pairs and 8% membrane fusion of unlabeled 3T3s, and subsequent washes with PEG resulted in up to 35% fluorescence exchange over CellTracker Green- and Red-labeled pairs and 25% membrane reorganization of unlabeled 3T3s. Viability staining with trypan blue performed on both unlabeled and labeled cells after fusion indicated an increase in cell death with additional washes with PEG, eventually limiting the effectiveness of subsequent doses.

Some devices were adapted to be compatible with electrofusion protocols. To introduce electric fields, the device was plasma-bonded to a glass slide containing metal electrodes (FIG. 5b). Once the cells were paired and immobilized, hypoosmolar fusion buffer was flowed past the cells, causing the cells to swell. The capture cups used were slightly deeper to accommodate the cells as they became larger. Again, as with the PEG protocol, the cells remained immobilized and paired as they changed size. An added benefit is that the cells were prealigned and in contact so no alternating current field was required. Membrane fusion was analyzed after the electrical pulse. It was found that electrofusion was significantly more efficient than PEG-mediated fusion ($P<0.05$); a single series of pulses yielded 78% fluorescence exchange over CellTracker-labeled red and green cell pairs and 89% membrane reorganization of unstained 3T3 cells.

Characterization of Cell Fusion

Figure 6:
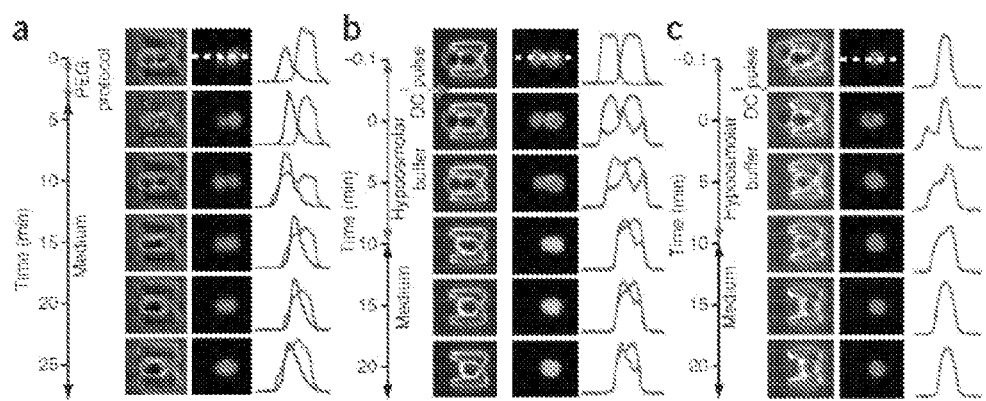
FIG. 6 is a Time course of chemical- and electric field-induced fusion for different cell pairs. (a) PEG fusion of GFP-expressing mESCs and Hoechst-stained mEFs. Phase-contrast images show the status of membrane reorganization and fluorescence overlay images and line-scans through the cells (dashed line) demonstrate the exchange of fluorescence Immediately before and after PEG addition, fluorescence was sequestered and two cell membranes were distinguishable. At t=10 min green fluorescence was observed inside the mEF, and at t=15 min the membranes began to reorganize. At t=25 min hybrids were observed that contained the contents of both cells. The mEF nucleus appeared to be intact (no fusion with nucleus of mESC). (b) Electrofusion of DsRed- and eGFP-expressing mouse 3T3s. Immediately after the fusion pulse, exchange of fluorescence was observed, outlining the nuclei of the cells. At t=10 min the membranes began to reorganize, and at t=20 min hybrid cells were observed that contained the contents of both cells. (c) Electrofusion of mouse B cells expressing GFP and unstained myeloma cells Immediately after the fusion pulse, GFP was observed in the properly loaded myeloma cell. The third cell in the capture cup was not aligned for fusion, therefore no exchange of fluorescence was observed and it falls off after t=5 min Membrane reorganization was difficult to observe, but at t=20 min only one cell membrane was observed.

Another advantage of our device is the ability to observe the progression of fusion at the single-cell level. Using PEG, we fused PEG GFP-expressing mESCs paired with Hoechst-stained mEFs in the device. Before and immediately after the PEG application, two distinct membranes were visible and fluorescence was still localized within each cell (FIG. 6). After 10 min, we observed green fluorescence within the mEF, demonstrating that the cytosols of the two cells had connected and fusion initiated. The Hoechst nuclear fluorescence was still localized in the mEF, indicating that the nucleus was intact. After 15 min, the plasma membranes began to reorganize, leading to a hybrid cell at t=25 min containing the contents of both cells. The Hoechst fluorescence remained partitioned in the new hybrid cell, suggesting no nuclear fusion had taken place. Electrofusion followed a different time course (FIG. 6b,c). Notably, fluorescence exchange was detected within seconds after the electric pulse, and in most cases, the outline of the nucleus was visible as the fluorescence first moved into the cytoplasm. This exchange of fluorescence was clear even though the cell membranes had yet to reorganize. After 10 min, the plasma membranes began to reorganize, and after 20 min, we observed hybrid cells. By immobilizing the cells, we could distinguish exchange of cell contents from membrane reorganization for single cell pairs.

Quantification of Fusion Over the Array

Immobilizing the cells in a dense array also provides the opportunity to observe fusion for thousands of cell pairs in parallel. Computational image analysis was used to monitor fluorescence exchange over the entire device in a fashion similar to a fluorescence-activated cell sorting (FACS) plot Immediately after the electrical pulse, the CellTracker-labeled red and green doubly fluorescent population increased to 53.5%. With increasing time, more cells exchanged fluorescence (maximum 63.9% at t=5 min) In addition, the amount of fluorescence exchanged also increased as shown by the CellTracker-labeled red and green doubly fluorescent cell populations located closer to the center of the plot. This indicates that connections are established that allow continual exchange and eventual equilibration of cytosolic material. Slight decreases in the number of doubly fluorescent cells at later times were artifacts owing to cells shrinking and moving out of the range of the analysis area.

Comparison of PEG Fusion with Electrofusion

Figure 7:
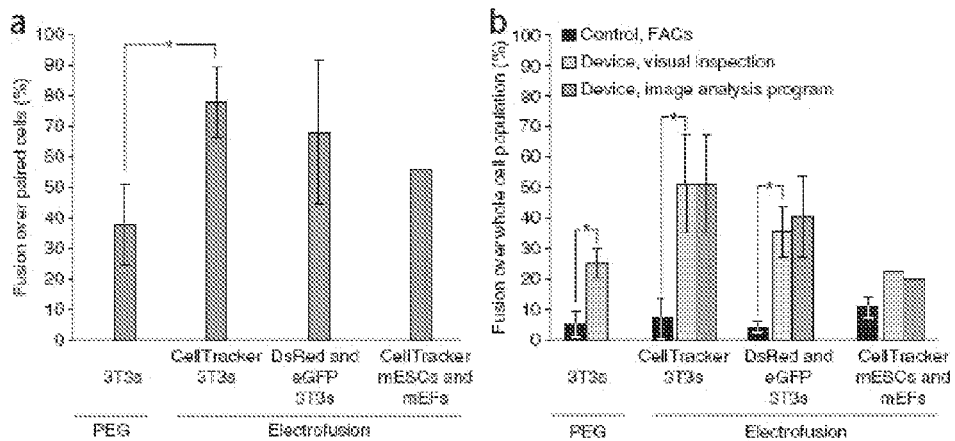
FIG. 7 is a Comparison of fusion efficiencies. (a) Comparison of PEG fusion efficiency using four doses of PEG and one dose of electrofusion in the microfluidic device as determined by visual inspection of the data. (b) Comparison of fusion efficiencies using the microfluidic device and controls. The values are based on red-green doubly fluorescent cells across the entire population or device. Control values were determined by FACS, and device values were determined by visual inspection and our image analysis program. The fusion values determined from the image analysis program agreed within error to those determined through manual inspection *P<0.05 (two-sided t-test). Error bars, s.d. (n=3).

The device allowed direct comparison of the fusion efficiencies of different fusion stimuli. PEG and electrofusion efficiencies were compared of properly paired cells determined by manually inspecting the images and evaluating the fluorescence exchange or membrane reorganization (FIG. 7a). Using PEG, PEG GFP-expressing mESCs paired with Hoechst-stained mEFs were fused in the device. Using PEG, fusion of 39%±14% of cell pairs was initiated, whereas electrofusion resulted in a significantly higher 78±12% fusion pairs ($P<0.05$). These electrofusion efficiencies were comparable to those obtained when DsRed-expressing and enhanced GFP (eGFP)-expressing cells were fused electrically in the device (68±24%, with a single-run high of 91%), and with CellTracker-stained mESCs and mEFs (single-run value of 56%). Cells were also placed in the device and cultured for 3 d (3 days) without fusion stimulus; no doubly fluorescent was observed (DsRed and eGFP) cells, indicating that negligible fusion occurred in the absence of fusogenic stimuli.

Comparison to Standard Macroscale Fusion Protocols

The overall efficiencies in generating fused cells with our device was compared to those with standard commercial PEG and electrofusion instruments and protocols. To compare between commercial and chip-based protocols, a common fusion metric of fluorescence exchange that could be assessed for all protocols and has been used by others was primarily used. Membrane reorganization for the on-chip PEG experiments was used. Fluorescence exchange was determined (percent red-green double-positive cells over the whole cell population) either by image-analysis program or by FACS and membrane reorganization was visually evaluated. Fusing CellTracker-labeled 3T3s using a standard PEG protocol yielded 6±4% fused cells, compared with a significantly higher 25±5% fused cells obtained after 4 doses of PEG in our micro-fluidic device ($P<0.05$; FIG. 7b). When electrofusion in a commercial system was compared to that in the microfluidic device, significantly higher fusion efficiencies were found in the microfluidic device ($P<0.05$). For Cell Tracker-labeled 3T3s, 11±9% fusion in the commercial Helix chamber (Eppendorf) was obtained as compared to 51±16% obtained in the microfluidic device of this invention, whereas for fluorescent protein-expressing 3T3s, 4±2% fused cells were obtained in the commercial electrofusion system and 40±13% in the microfluidic device. Finally, 11±4% electrofusion of CellTracker-labeled mESCs and mEFs was obtained in the commercial system, and 23% electrofusion with the microfluidic device (single run). In all cases, use of the microfluidic device delivered a two-fold to tenfold improvement in fusion yield compared to commercial systems.

Demonstration of Functionality of Fused Cells

Next, to determine whether cells removed from the chip after fusion can survive prolonged culture, 3T3s were removed after fusion in the device and cultured for 10 d (10 days). Viable fused cells were obtained as determined by the presence of red-green double-positive cells (FIG. 8a,b), and via FACS analysis.

Figure 8:
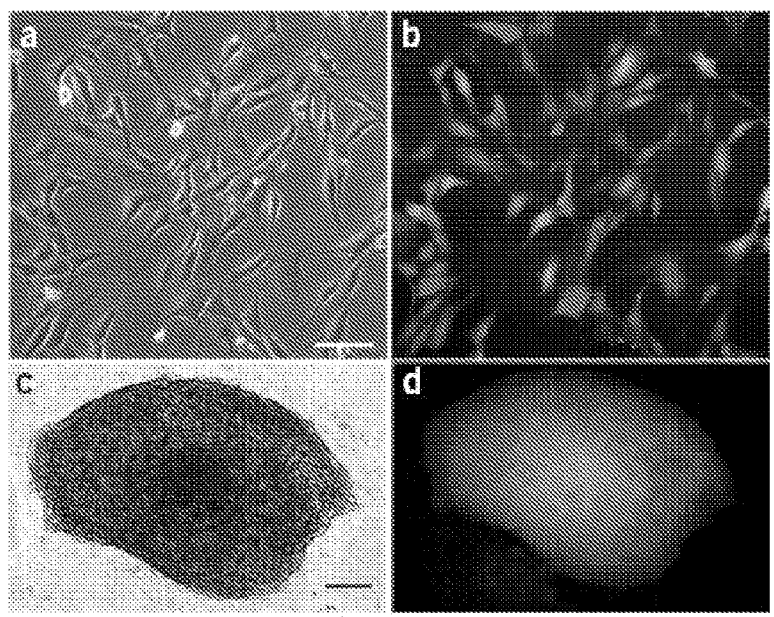
FIG. 8 demonstrates functionality of fused cells. (a,b); Phase-contrast (a) and fluorescence image (b) of DsRed-eGFP 3T3s at day 4 after fusion in the microfluidic device indicating the presence of red-green double-positive fused cells. (c,d) Analyzing only the properly paired red and green cells allowed a direct comparison of chemical versus electrical fusion independent of capture and pairing efficiency. Scale bars, 100 µm.

Fusions of embryonic stem cells with somatic cells have been previously used to demonstrate the capability of embryonic stem cells to reprogram somatic cells. To show that the microfluidic device can also be used to generate viable hybrids between mESCs and mEFs, Hygromycin-resistant mESCs were fused with Puromycin-resistant mEFs in the device and cultured under self-renewing conditions. After 14 d (14 days) under double selection, drug-resistant colonies were observed that had an embryonic stem cell-like morphology and expressed alkaline phosphatase (FIG. 8c). Reactivation of embryonic genes, such as Nanog and Oct4, has been used to demonstrate successful reprogramming of somatic cells. The Puromycin-resistant mEFs carried an additional Oct4-GFP reporter in their endogenous Oct4-locus, allowing to investigate whether reprogramming, as judged by the reactivation of Oct4-GFP, would also occur. Colonies expressing alkaline phosphatase that also expressed GFP were detected, demonstrating that the device is suitable for generating viable hybrids and observing reprogramming of mEFs after fusion with mESCs (FIG. 8d).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A particle patterning device comprising:
a first substrate;
at least one capture unit positioned such that the top of said capture unit is adhered to or contiguous with said first substrate, said capture unit comprising:
a first chamber comprising at least one opening, sized to trap and accommodate a single particle; and
a second chamber comprising at least one opening, sized to trap and accommodate a single or more than a single particle;
wherein an opening of said first chamber faces a direction opposite to that of an opening of said second chamber, and said opening of said first chamber is contiguous with a side of said capture unit, said opening of said second chamber is contiguous with an opposite side of said capture unit;
a second substrate positioned proximally to or adhered to a bottom of said capture unit or a portion thereof;
a first conduit through which a first flow is induced in said device, such that said first flow is accommodated at least between said capture unit and said second substrate and particles positioned within said first or second chamber are subject to said first flow, wherein said first conduit, said capture unit, and said second substrate are configured to accommodate said first flow in a direction towards the opening of the first chamber; and
a second conduit through which a second flow is induced in a direction opposite to that of said first flow and towards the opening of the second chamber, such that said second flow is accommodated at least between said capture unit and said second substrate and particles positioned within the first or second chamber are subject to said second flow.

2. The particle patterning device of claim 1, further comprising at least one supporting structure positioned between said first and said second substrate, which aids in suspending said capture unit over said second substrate, at a height sufficient to accommodate fluid flow between said second substrate and said capture unit.

3. The particle patterning device of claim 2, wherein said at least one supporting structure is proximal to or contiguous with at least a portion of said capture unit.

4. The particle patterning device of claim 1, wherein said first chamber, said second chamber, or a combination thereof comprise at least one additional opening, which is sized such that said opening cannot trap or accommodate one or more particles.

5. The particle patterning device of claim 4, wherein said additional opening is positioned between said first and second chamber such that said opening facilitates fluid communication between said first and said second chamber.

6. The particle patterning device of claim 1, further comprising controllers to maintain desirable environmental conditions.

7. The particle patterning device of claim 6, wherein said controllers maintain a desired temperature, pH, $CO_2$ or Oxygen conditions, or a combination thereof.

8. The particle patterning device of claim 1, wherein said device is comprised of a transparent material.

9. The particle patterning device of claim 8, wherein said transparent material is pyrex, quartz, Polydimethylsiloxane (PDMS) or SU-8.

10. The particle patterning device of claim 1, further comprising electric connections between said first capture unit, said second capture unit or a combination thereof and a power supply.

11. The particle patterning device of claim 1, wherein said device is a microfluidic device.

12. The particle patterning device of claim 1, wherein said first chamber has a width ranging from between 5-500 μm and a depth ranging from between 5-500 μm.

13. The particle patterning device of claim 12, wherein said first chamber has a width of about 10 μm and a depth of about 5 μm.

14. The particle patterning device of claim 1, wherein said second chamber has a width ranging from between 5-500 μm and a depth ranging from between 5-500 μm.

15. The particle patterning device of claim 14, wherein said second chamber has a width of about 10 μm to about 35 μm and a depth of about 5.5 μm to about 50 μm.

16. The particle patterning device of claim 1, comprising an array of capture units.

17. The particle patterning device of claim 16, wherein said array is arranged in a row or column scheme or a combination thereof.

18. The particle patterning device of claim 17, wherein said scheme comprises a spacing between said row or column or combination thereof, said spacing approximate in width to a diameter of a particle being applied to said device.

19. The particle patterning device of claim 17, wherein said scheme comprises asymmetrically positioning a capture unit in a first row off-set from that of a capture unit in a preceding or subsequent row.

20. The particle patterning device of claim 19, wherein said off-set is half the center-to-center distance between two capture units.

21. An apparatus comprising the particle patterning device of claim 1.

22. The apparatus of claim 21, wherein an illumination source is coupled to said device.

23. The apparatus of claim 22, wherein the illumination source is a laser.

24. The apparatus of claim 22, wherein a beam splitter is employed with the use of said illumination source.

25. The apparatus of claim 21, further comprising a detector, which detects a change in a parameter in said device.

26. The apparatus of claim 25, wherein said detector comprises a camera, a computer, a luminometer, a spectrophotometer, or a combination thereof.

27. A method for patterning individual particles, said method comprising:
(i) applying a first liquid comprising a series of first particles to a particle patterning device under flow in a first direction, whereby an individual particle is accommodated within a first capture unit of said particle patterning device, said device comprising:
a first substrate;
at least one capture unit positioned such that the top of said capture unit is adhered to or contiguous with said first substrate, said capture unit comprising:
a first chamber comprising at least one opening, sized to trap and accommodate a single particle; and
a second chamber comprising at least one opening, sized to trap and accommodate a single or more than a single particle;
wherein an opening of said first chamber faces a direction opposite to that of an opening of said second chamber, and said opening of said first chamber is contiguous with a side of said capture unit, said opening of said second chamber is contiguous with an opposite side of said capture unit;
a second substrate positioned proximally to or adhered to a bottom of said capture unit or a portion thereof;
a first conduit through which a first flow is induced in said device, such that said first flow is accommodated at least between said capture unit and said second substrate and particles positioned within said first or second chamber are subject to said first flow, wherein said first conduit, said capture unit, and said second substrate are configured to accommodate said first flow in a direction towards the opening of the first chamber; and
a second conduit through which a second flow is induced in a direction opposite to that of said first flow and towards the opening of the second chamber, such that said second flow is accommodated at least between said capture unit and said second substrate and particles positioned within the first or second chamber are subject to said second flow; and
(ii) applying a second liquid to said device under flow in a second direction, wherein said individual particle moves from said first chamber of said first capture unit to a second chamber in a second capture unit.

28. The method of claim 27, wherein said particle patterning device comprises an array of capture units positioned in rows or columns or a combination thereof.

29. The method of claim 27, further comprising the step of applying a third liquid comprising a series of second particles to said device under flow in said second direction, whereby said series of second particles are patterned in said second chamber in a said second capture units with said series of first particles.

30. The method of claim 27, further comprising the step of applying a third liquid to said device under flow in said first direction, whereby said individual particle moves back to said first chamber in said first capture unit.

31. The method of claim 29, wherein said series of first particles, second particles or a combination thereof are cells, vesicles, or microspheres, or a combination thereof.

32. The method of claim 31, wherein said cells are mammalian cells, bacterial cells, parasitic cells, yeast cells or a combination thereof.

33. The method of claim 31, wherein said series of first particles and said series of second particles comprise cells of a similar cell type or are of, or isolated from, the same organism.

34. The method of claim 31, wherein said series of first particles and said series second particles comprise cells of a different cell type or are of, or isolated from, a different organism.

35. The method of claim 31, wherein said cells comprise a vector, which optionally comprises a reporter.

36. The method of claim 31, wherein said method is a fusion method between said cells, vesicles, or microspheres, or a combination thereof.

37. The method of claim 27, wherein said method further comprises applying a reagent to said device under flow in said second direction.

38. The method of claim 37, wherein said reagent is for detection, assay or a combination thereof of said series of first particles, second particles or a combination thereof.

39. The method of claim 37, wherein said reagent comprises a detectable marker.

40. The method of claim 29, wherein said series of first particles and said series of second particles are of the same size.

41. The method of claim 29, wherein said series of first particles and said series of second particles differ in size, composition, or a combination thereof.

42. The method of claim 29, further comprising the step of observing said series of first particles and said series of second particles over a course of time.

43. The method of claim 27, wherein said device is maintained under controlled temperature, pH, $CO_2$ or Oxygen conditions, or a combination thereof.

44. A method of contacting individual particles, said method comprising:
(i) applying a first liquid comprising a series of first particles to a particle patterning device under flow in a first direction, whereby an individual particle is accommodated within a first chamber in a first capture unit of said particle patterning device, said device comprising:
a first substrate;
at least one capture unit positioned such that the top of said capture unit is adhered to or contiguous with said first substrate, said capture unit comprising:
a first chamber comprising at least one opening, sized to trap and accommodate a single particle; and
a second chamber comprising at least one opening, sized to trap and accommodate a single or more than a single particle;
wherein an opening of said first chamber faces a direction opposite to that of an opening of said second chamber, and said opening of said first chamber is contiguous with a side of said capture unit, said opening of said second chamber is contiguous with an opposite side of said capture unit;
a second substrate positioned proximally to or adhered to a bottom of said capture unit or a portion thereof;
a first conduit through which a first flow is induced in said device, such that first flow is accommodated at least between said capture unit and said second substrate and particles positioned within said first or second chamber are subject to said first flow, wherein said first conduit, said capture unit, and said second substrate are configured to accommodate said first flow in a direction towards the opening of the first chamber such that a single particle introduced under flow is trapped within the first chambers; and a second conduit through which a second flow is induced in a direction opposite to that of said first flow and towards the opening of the second chamber, such that said second flow is accommodated at least between said capture unit and said second substrate and particles positioned within the first or second chamber are subject to said second flow; and (ii) applying flow in a second direction, wherein said individual particle moves from said first chamber of said first capture unit to a second chamber in a second capture unit; and (iii) applying a second liquid comprising a series of second particles to said device in said second direction, whereby said second particles positioned within said second chamber are brought into contact with said series of first particles, thereby being a method of contacting individual particles.

45. The method of claim 44, wherein bringing said first and second series of particles into contact results in a transfer of a material from one particle to another.

46. The method of claim 44, wherein said material comprise a biological material.

47. The method of claim 46, wherein said material is a nucleic acid or polypeptide.

48. The method of claim 44, wherein said particle is a cell.

49. The method of claim 48, wherein said method results in genetic transformation of said cell.

50. The method of claim 44, wherein said first or second series of particles or a combination thereof are cells.

51. The method of claim 50, wherein said method comprises a method of cell fusion.

52. The method of claim 50, wherein said method comprises a method of single cell infection.

53. The method of claim 50, wherein said method comprises a method of phagocytosis.

54. The method of claim 44, wherein bringing said first and said second series of particles into contact results in a measurable energy transfer.

55. The method of claim 54, wherein said energy transfer is fluorescent resonance energy transfer (FRET).

56. The method of claim 44, wherein said method comprises a screen for molecular interactions.

* * * * *